(12) United States Patent
Lafferty, IV

(10) Patent No.: US 7,753,890 B2
(45) Date of Patent: Jul. 13, 2010

(54) MULTIPLE DRUG INJECTION APPARATUS

(75) Inventor: John Peter Lafferty, IV, Miami Beach, FL (US)

(73) Assignee: Dragon Drug Gun, Inc., Miami Beach, FL (US)

( * ) Notice: Subject to any disclaimer, the term of this patent is extended or adjusted under 35 U.S.C. 154(b) by 440 days.

(21) Appl. No.: 11/764,221

(22) Filed: Jun. 17, 2007

(65) Prior Publication Data

US 2008/0171996 A1     Jul. 17, 2008

Related U.S. Application Data

(63) Continuation-in-part of application No. 11/610,930, filed on Dec. 14, 2006.

(51) Int. Cl.
*A61M 5/00*     (2006.01)
*A61M 5/30*     (2006.01)
*A61M 5/178*     (2006.01)

(52) U.S. Cl. ..................... 604/191; 604/183; 604/68

(58) Field of Classification Search ............... 604/110, 604/191, 68
See application file for complete search history.

(56) References Cited

U.S. PATENT DOCUMENTS

| | | | |
|---|---|---|---|
| 2,168,686 A | * | 8/1939 | Saffir ......................... 604/415 |
| 3,563,240 A | * | 2/1971 | Silver .......................... 604/87 |
| 4,367,737 A | * | 1/1983 | Kozam et al. ................ 604/191 |
| 4,790,823 A | * | 12/1988 | Charton et al. .............. 604/136 |
| 5,354,284 A | * | 10/1994 | Haber et al. ................. 604/191 |
| 5,411,485 A | * | 5/1995 | Tennican et al. ............ 604/191 |
| 6,056,716 A | * | 5/2000 | D'Antonio et al. ............ 604/68 |
| 6,508,791 B1 | * | 1/2003 | Guerrero ..................... 604/183 |
| 2003/0040700 A1 | * | 2/2003 | Hickle et al. ................... 604/67 |
| 2006/0032501 A1 | * | 2/2006 | Hale et al. ............. 128/203.12 |
| 2008/0045925 A1 | * | 2/2008 | Stepovich et al. ........... 604/518 |
| 2008/0214996 A1 | * | 9/2008 | Kimmell et al. ............... 604/68 |
| 2008/0221602 A1 | * | 9/2008 | Kuehner et al. ............. 606/167 |

* cited by examiner

*Primary Examiner*—Nicholas D Lucchesi
*Assistant Examiner*—Ian K Holloway
(74) *Attorney, Agent, or Firm*—Albert Bordas, P.A.

(57) ABSTRACT

A fluid dispensing device, particularly suited to medicine but also having many other applications. The device selectively dispenses any of one or more fluids contained within the device. Adapters on the dispensing end of the unit permit the device to be effectively used for intra-venous, intra-dermal or intramuscular injections, gasses, colloids, gels, liquids or other fluids. Adapters on the head of the unit permit the device to be used with or without electrical power and to varying degrees of automatic control for timing, sequence, volume of fluid dispensed and other features. A preferred embodiment utilizes a pre-formatted, disposable or re-useable cartridge of several drugs suited for a particular medical purpose.

2 Claims, 24 Drawing Sheets

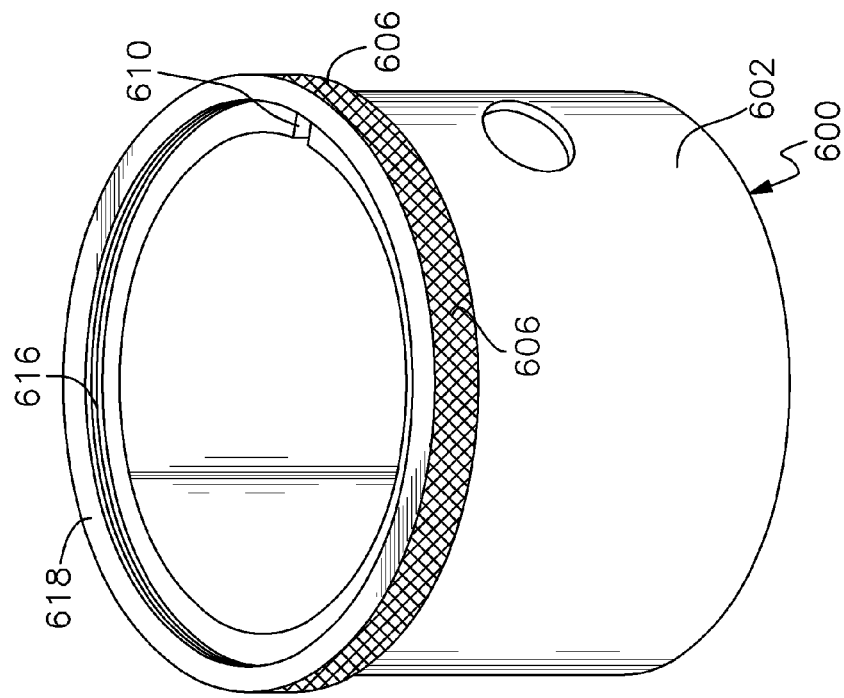
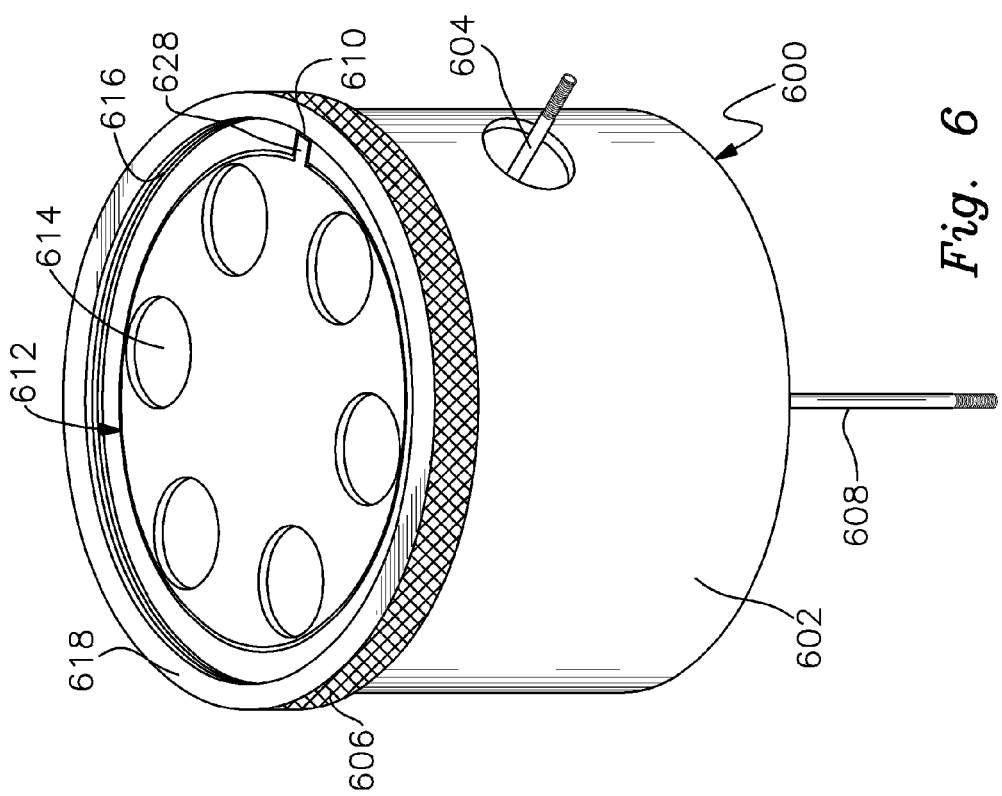

MULTIPLE DRUG INJECTION APPARATUS

OTHER RELATED APPLICATIONS

The present application is a continuation-in-part pending of U.S. patent application Ser. No. 11/610,930, filed on Dec. 14, 2006, which is hereby incorporated by reference.

BACKGROUND OF THE INVENTION

1. Field of the Invention

The present invention relates to fluid dispensers, and more particularly, to a fluid dispenser that, in one of the preferred embodiments, is suited to dispense drugs.

2. Description of the Related Art

Several designs for fluid dispensers have been designed in the past. None of them, however, includes a means to selectively dispense fluids in a precise volume.

Applicant believes that the closest reference corresponds to U.S. patent application Ser. No. 11/156,575 by inventor Wesley Verkaart. However, it differs from the present invention because the Verkaart invention does not provide a means to precisely dispense liquids, does not have a triggering mechanism, does not provide a means to reduce mixing of the dispensed fluids, has no automatic or electrical features, requires greater user skill when used to deliver drugs and does not provide a means to inject at a specific needle depth, all of which are provided for in the present invention.

Other patents describing the closest subject matter provide for a number of more or less complicated features that fail to solve the problem in an efficient and economical way. None of these patents suggest the novel features of the present invention.

SUMMARY OF THE INVENTION

The instant invention is a fluid dispensing device comprising a head assembly comprising one or more shafts that controllably extend and retract and a means to power and control said shafts; a case assembly that comprises one or more vessels that contain fluid where said shaft can selectively exert force onto a vessel thereby expelling said fluid from the vessel; and a manifold assembly that channels the dispensed fluid from each of said vessels through a common output. The fluid dispensing device may be further characterized in that said means to power said head assembly is springs, pneumatic cylinders or electronic lineal actuators. The fluid dispensing device may be further characterized in that said vessels are unified into a cartridge removable from said case assembly. The fluid dispensing device may be further characterized in that the fluid dispensation is computer controlled. The fluid dispensing device may be further characterized in that said manifold assembly has a port for an external fluid source to flush through said manifold assembly. The fluid dispensing device may be further characterized in that one way valves are between each of said vessels and said manifold assembly. The fluid dispensing device may be further characterized in that a mechanical means to stop fluid dispensation at a selectable volume is present. A method of using the fluid dispensing device may be further characterized in that the fluids dispensed are drugs pre-selected for a specific medical procedure. A method of using the fluid dispensing device may be further characterized where the fluids dispensed are lubricants, food products, gasses, liquids, chemical reagents, tints, colorants, stains, paints or gels. The fluid dispensing device may be further characterized in that said manifold assembly includes a bubble trap.

The instant invention is alternatively a fluid dispensing device comprising a head assembly comprising a means to select a fluid to be dispensed and a means to dispense a fluid; a case assembly that contains one or more vessels containing fluid to be dispensed; a manifold assembly that channels the fluids to be dispensed through a common output port. The alternate fluid dispensing device may also be further characterized in that said means to power said head assembly is a spring, pneumatic cylinder or electronic lineal actuator. The alternate fluid dispensing device may also be further characterized in that said vessels are unified into a cartridge removable from said case assembly. The alternate fluid dispensing device may also be further characterized in that the fluid dispensation is computer controlled. The alternate fluid dispensing device may also be further characterized in that said manifold assembly has a port for an external fluid source to flush through said manifold assembly. The alternate fluid dispensing device may also be further characterized in that one way valves are between each of said vessels and said manifold assembly. The alternate fluid dispensing device may also be further characterized in that a mechanical means to stop fluid dispensation at a selectable volume is present.

The instant invention is alternatively a case that contains multiple fluids each in a vessel, a means to select a fluid to be dispensed and a manifold assembly to direct each fluid from said vessel through a common output port. The alternate fluid dispensing device may also be further characterized in that said means to power said head assembly is a spring, pneumatic cylinder or electronic lineal actuator. The alternate fluid dispensing device may also be further characterized in that said vessels are unified into a cartridge removable from said case assembly. The alternate fluid dispensing device may also be further characterized in that one way valves are between each of said vessels and said manifold assembly.

It is therefore one of the main objects of the present invention to provide a device that contains fluid that can be dispensed quickly.

It is another object of this invention to provide a device that can reduce human error in the dispensing of fluid.

It is an object of this invention to provide a compact and efficient fluid dispensing device.

It is an object of this invention to reduce waste and costs associated with storage and disposal of waste.

It is an object of this invention to provide a device that permits a reduced time to change between fluids dispensed.

It is an object of this invention to permit rapid re-loading of fluid in a safe and efficient manner.

It is an object of this invention to have a device that can dispense various fluids common to a particular application of use.

It is still another object of the present invention to provide a device that can be used effectively and safely, in certain embodiments, for emergency medicine, combat medicine, first responders, anesthesiology, dentistry, veterinary medicine and many medical situations.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 6 is a perspective view of an embodiment of a manifold cartridge assembly nested inside a manifold assembly.

FIG. 7 illustrates a perspective view of an embodiment of a manifold assembly without a cartridge assembly.

DETAILED DESCRIPTION OF THE PREFERRED EMBODIMENT

Figure 1:
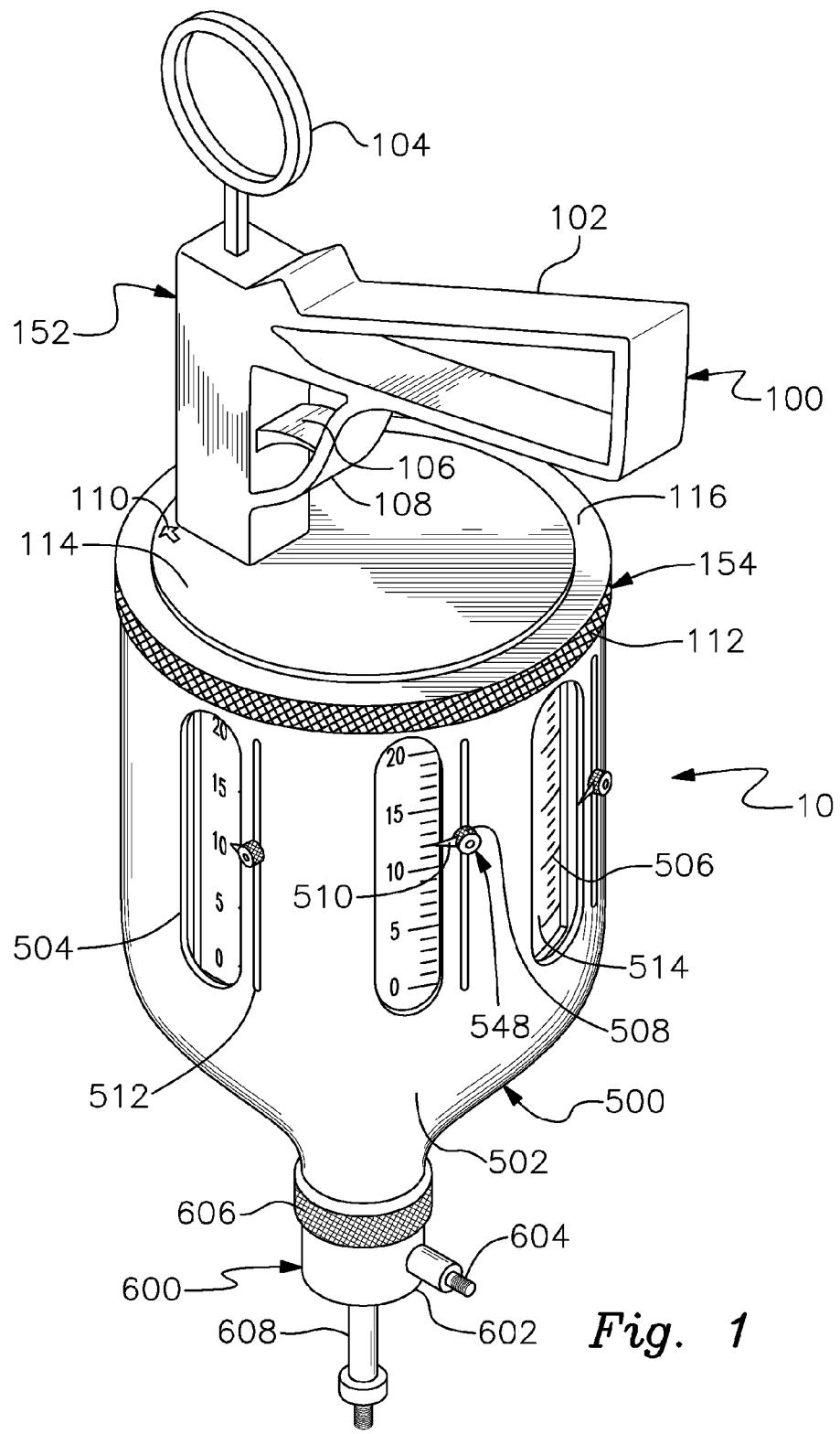
FIG. 1 represents a perspective view of an embodiment of the invention.

Referring now to the drawings, where the present invention is generally referred to with numeral 10, it can be observed in FIG. 1 that in this embodiment it basically includes a manual head assembly 100, a case assembly 500 and a manifold assembly 600.

Referring to FIG. 1 an embodiment of said manual head assembly 100 is shown to comprise, inter alia, a handle assembly 152 and a head cap assembly 154. Said handle assembly 152, comprises, inter alia, a handle 102, a cocking lever 104, a trigger 106, a trigger guard 108 and an indicator 110.

Said cocking lever 104 is drawn away from said manual head assembly 100 to input energy into the invention to be subsequently used to dispense fluid from the device. Said trigger 106 is depressed to activate the dispensing of a fluid. The trigger 106 is protected from inadvertent activation by the protective trigger guard 108.

Said handle 102 generally conforms to the shape of a human hand to facilitate ergonomic use of the device. As an optional feature, said handle 102 may be open to form a loop that can be used to lighten the device as well as provide a feature to secure the device in storage or while in use. For example, the invention could be hung onto a hook through the handle 102 for storage.

Still referring to FIG. 1, said head cap assembly 154 is comprised of, inter alia, a crown 116 with a knurled grip 112. The handle assembly 152 is rotatably connected to the head cap assembly 154. As described in more detail below, a fluid contained inside the device can be selected for output by applying force to the handle assembly 152 through the handle 102 effecting rotation of the handle assembly 152 relative to the head cap assembly 154. An indicator 110 affixed to a turntable 114 that is part of the handle assembly 152 provides an aid to determine which fluid is selected for dispensing. The knurled grip 112 of the head cap assembly 154 aids the user assemble the device by providing a gripping surface to thread the manual head assembly 100 onto said case assembly 500 thus forming a unitary body.

As seen FIG. 1, said case assembly 500 is comprised of, inter alia, a case 502, one or more viewing ports 504 and a thumb lock assembly 548 that is further comprised of, inter alia, a thumb lock 508, an indicator 510 and a guide 512, each described in more detail below. In one contemplated embodiment, the case assembly 500 contains a vessel 514 that can be partially seen in FIG. 1 through one or more viewing ports 504 to show graduations 506 to determine the volume of fluid contained in the vessel(s) 514.

Again referring to FIG. 1, exterior portions of one of several contemplated embodiments of a manifold assembly 600 is shown to comprise, inter alia, a manifold cap 602, a fluid port 604, a knurled grip 606 and another fluid port 608, each described in more detail below.

Figure 2:
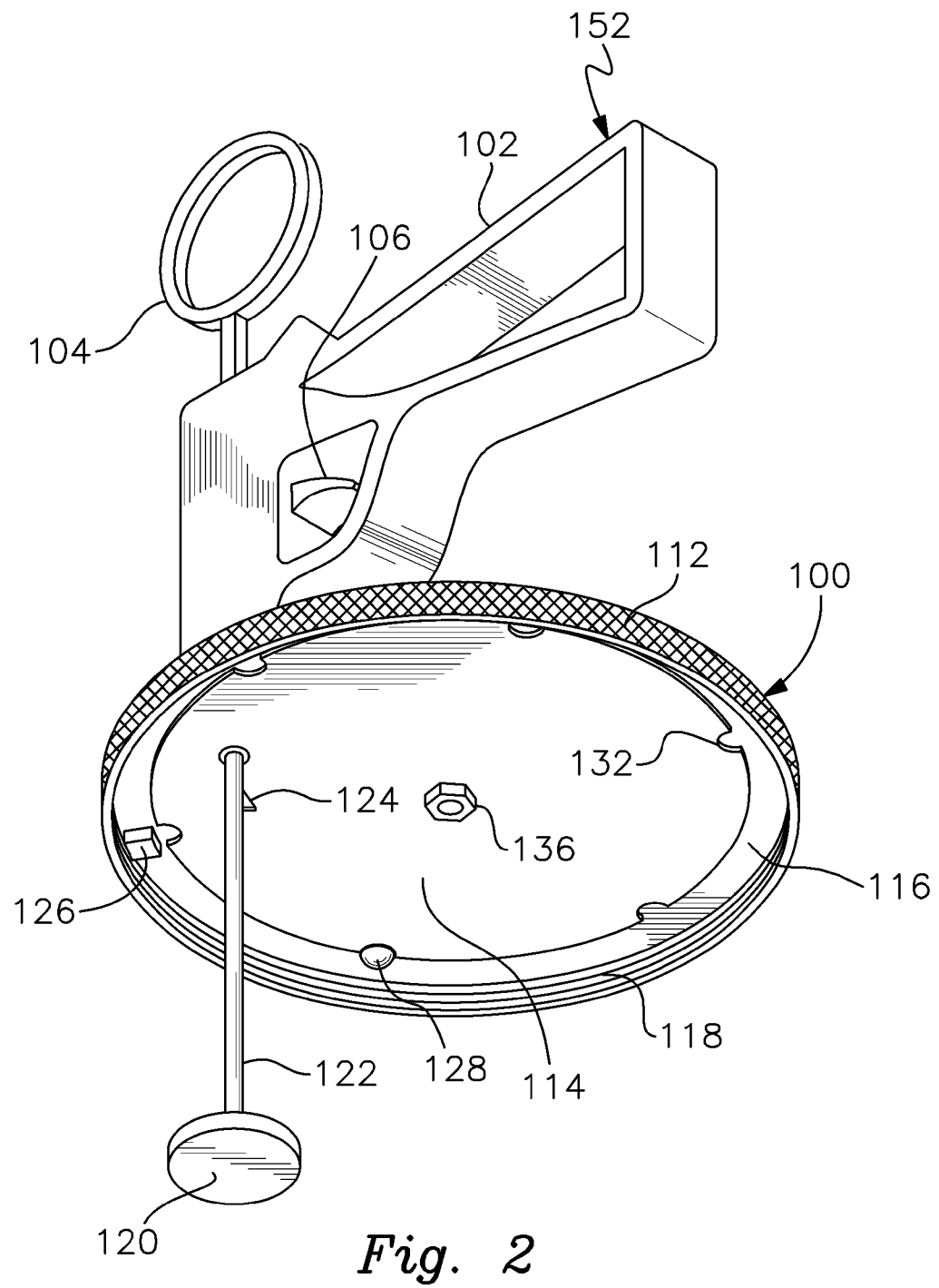
FIG. 2 shows a perspective view of an embodiment of a manual head assembly.

Now referring to FIG. 2 where the underside of the manual head assembly 100 is shown in more detail. In this embodiment of the device the handle assembly 152 is affixed to the turntable 114 by means of a nut 136, but other means could similarly be used. For example, the handle assembly 152 could be welded to the turntable 114 or be formed from the same unitary material as the turntable 114.

Also shown in FIG. 2 is a knurled grip 112 to provide greater grip when the user assembles or disassembles the device. Threads 118 provide a means to connect the manual head assembly 100 to the case assembly 500. Other means to connect the manual head assembly (or the other head assemblies described below) could include, inter alia, any of a wide variety of known and commonly used clips, snaps, brackets, straps, adhesives, welds, rivets, screws or other similar means. A key 126 is located in a predetermined position superior to the threads 118 and engages into a key slot 530 (shown on FIG. 4) on the case assembly 500 to ensure that the mechanics of the mechanical head assembly 100 align with the case assembly 500 with adequate precision.

Still referring to FIG. 2, a plunger 120 affixed to a shaft 122 is shown. The shaft 122 is movable axially through the turntable 114. Said shaft 122 and plunger 120 are part of the handle assembly 152. One of the handle assembly's 152 functions is to provide a means to move the shaft 122, and thereby the plunger 120, axially through the turntable 114. In this embodiment the shaft 122 also has a stop 124 that interacts with the thumb lock assembly 548 (shown in more detail in FIG. 10 and described below) as one of the contemplated means to regulate the volume of fluid dispensed.

Yet referring to FIG. 2, a spring button 128 and a notch 132, among other components, interact to provide a means to affirmatively select the rotational position of the turntable 114, and thereby the handle assembly 152, relative to the key 126 on the crown 116. As the turntable 114 rotates relative to the crown 116 the spring button 128 encounters and frictionally engages a notch 132. One or more notches 132 are arranged at predetermined positions on the turntable 114 to provide precise alignment of the plunger 120 relative to the key 126. This is but one way to affirmatively select a position. Other suitable means to affirmatively select a position are commonly used in industry.

Figure 3:
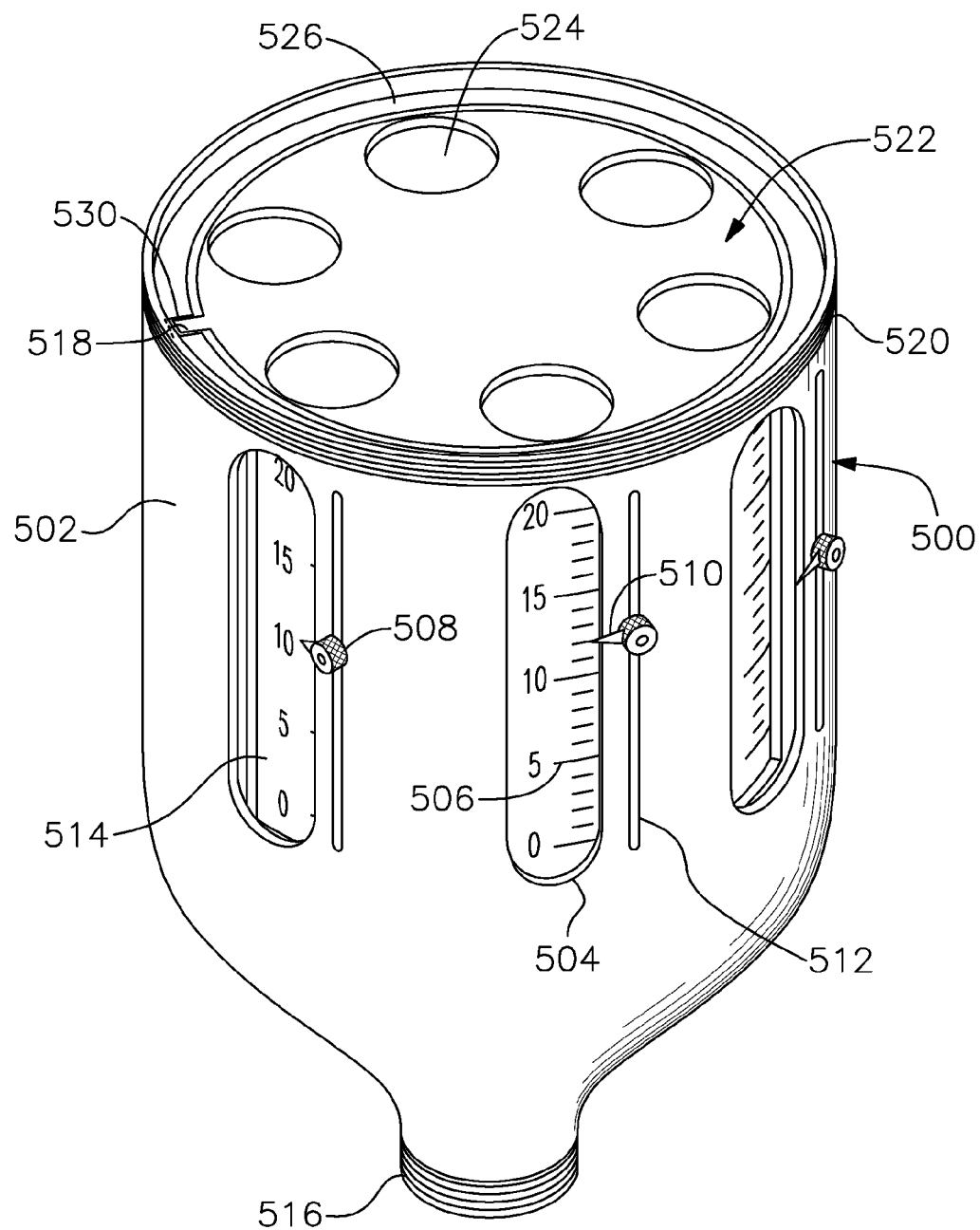
FIG. 3 illustrates a perspective view of an embodiment of a cartridge assembly nested inside a case assembly.

FIG. 3 illustrates one embodiment of the case assembly 500 with a cartridge assembly 522 fitted inside the case assembly 500. In this view of the cartridge assembly a vessel 514, a piston 524 and a key 518 are visible. The vessel 514 is generally cylindrical and is seen through a viewing port 504 on the side of the case assembly 500. The piston 524 is generally cylindrical and slidably engaged inside of the vessel 514. The vessel 514 is sealed by the piston 524. In one contemplated embodiment the vessel 514 and piston 524 is similar to a commonly used medical syringe. When the device is dispensing fluid the plunger 120 (illustrated in FIG. 2) applies force to the surface of the piston 524 and the piston 524 is forced downward axially along the interior of the vessel 514. The key 518 on the cartridge assembly 522 mates with a key slot 530 of the case assembly 500 to ensure proper orientation of the cartridge assembly 522 to the case assembly 500.

Still referring to FIG. 3, some features of the case assembly are visible including, inter alia, the case 502, a seat 526, threads 520, a key slot 530, an indicator 510, a thumb lock 508, a guide 512 and threads 516. The threads 520 engage the threads on the manual head assembly 100 or other embodiments of various head assemblies, infra. Said manual head assembly 100 contacts the case assembly at said seat 526. The threads 516 engage the threads 616 on the manifold assembly 600 (shown in FIG. 6) or other embodiments of various manifold assemblies, infra.

Figure 4:
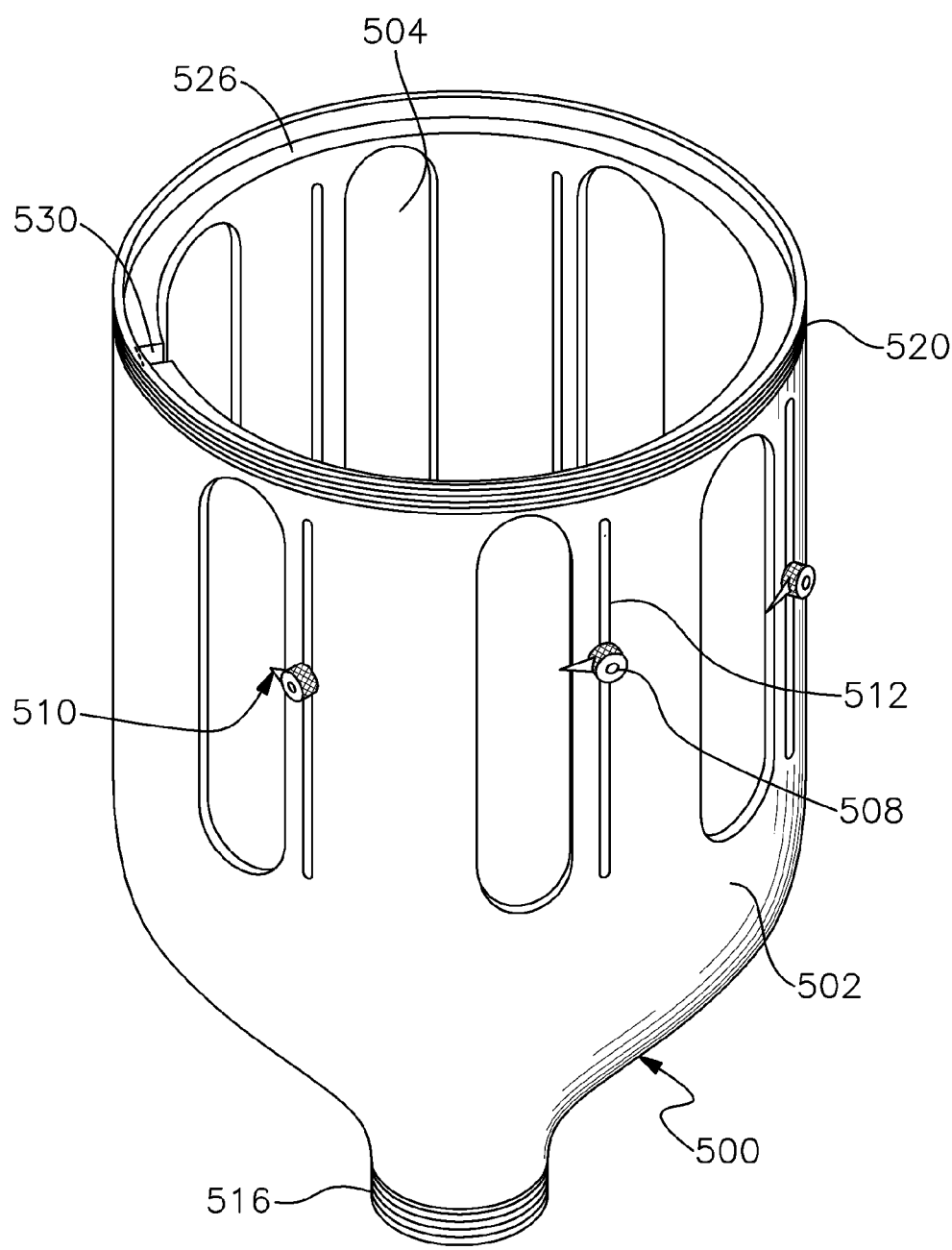
FIG. 4 is a representation of a perspective view of an embodiment of a case assembly.

FIG. 4 depicts the case assembly 500 without the cartridge assembly 522 as is present in FIG. 3. With the cartridge assembly removed the viewing ports 504 are shown around the periphery of the case assembly 500. The number of viewing ports 504 would typically be commensurate with the number of vessels 514 (absent in FIG. 4 and shown in FIG. 5).

Figure 5:
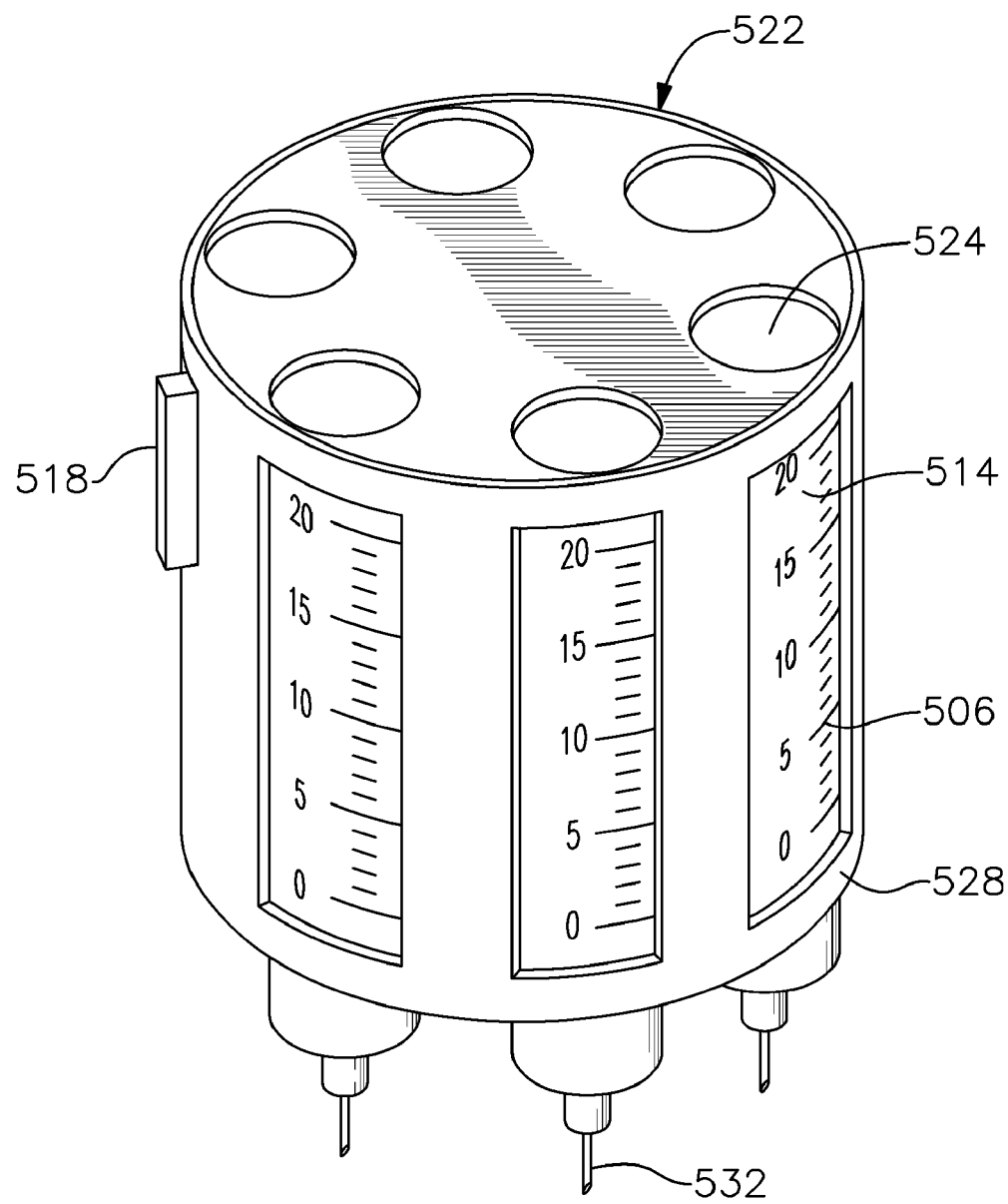
FIG. 5 is a perspective view of an embodiment of a cartridge assembly.

FIG. 5 is an illustration of one contemplated embodiment of a cartridge assembly 522 that comprises, inter alia, a frame 528, a vessel 514, graduations 506, piston 524, vessel port 532 and key 518. Said frame 528 provides the structure to hold one or more vessels 514 fixed relative to one another. Said key 518 is positioned at a predetermined location on the frame 528 and is dimensioned to engage the key slot 530 on the cartridge assembly 522 (shown on FIG. 4) at a precise relative orientation. An optional, but desirable, feature on each vessel 514 are graduations 506 to aid the user to more precisely measure the volume of fluid dispensed. Generally, the graduations 506 are readable through a viewing port 504 (as shown in FIG. 3). The graduations 506 would typically show the remaining volume of fluid contained in the vessel 514 in milliliters or cubic centimeters as indicated by reading the position of the bottom of the piston 524 relative to the graduations 506. Said vessel port 532 is the path by which the fluid contained in the vessel 514 exits the vessel 514 during dispensing. Vessel port 532 can also be where fluid is drawn back into the vessel 514 when refilling the vessel 514. In one of the preferred embodiments the vessel 514 is a common syringe and the vessel port 532 is a common hypodermic needle affixed to the lower end of the vessel 514.

Referring now to FIG. 6 where one of the embodiments of a manifold assembly 600 is shown that is comprised of, inter alia, a manifold cap 602, a fluid port 604, a knurled grip 606, a fluid port 608, a key slot 610, a septum 614, threads 616, a seat 618 and a manifold cartridge assembly 612. When in typical use said manifold assembly 600 is threaded onto the case assembly 500 by means of threads 616 on the manifold assembly 600 engaging the threads 516 on the case assembly 500 and rests on the seat 618. A knurled grip 606 aids the user when threading the pieces together. Other contemplated means to secure the case assembly 500 to the manifold assembly 600 (or other embodiments of manifold assemblies) could include, inter alia, any of a wide variety of known and commonly used clips, snaps, brackets, straps, adhesives, welds, rivets, screws or other similar means.

Still referring to FIG. 6, the manifold cartridge assembly 612 is nested in the manifold assembly 600. The orientation of the manifold cartridge assembly 612 with the manifold cap 602 is maintained by aligning a key 628 on the manifold cartridge assembly 612 in the key slot 610 on the manifold assembly 600. The top of the manifold cartridge assembly 612 may have a septum 614 capable of receiving said vessel port 532 (shown in FIG. 5) and making a leak resistant union. For example, if the vessel port 532 was similar in form to a common hypodermic needle then the septum 614 could be made of a rubber-like material that a hypodermic needle could readily puncture and maintain a leak-resistant seal. Other means to connect the manifold cartridge assembly 612 to the vessel port 532 can be easily improvised from a wide variety of medical and industrial connectors readily available.

FIG. 7 shows an embodiment of the manifold assembly 600 without the manifold cartridge assembly 612. Shown in this view is, inter alia, the knurled grip 606 to give the user better grip when attaching the manifold assembly 600 to the case assembly 500 by means of the threads 616 on the manifold assembly 600 and the threads on the case assembly 516. Other contemplated means to secure the case assembly 500 to the manifold assembly 600 (or other embodiments of a manifold assembly) could include, inter alia, any of a wide variety of known and commonly used clips, snaps, brackets, straps, adhesives, welds, rivets, screws or other similar means. A seat 618 provides a stable surface for the case assembly 500 to contact the manifold assembly 600.

Figure 8:
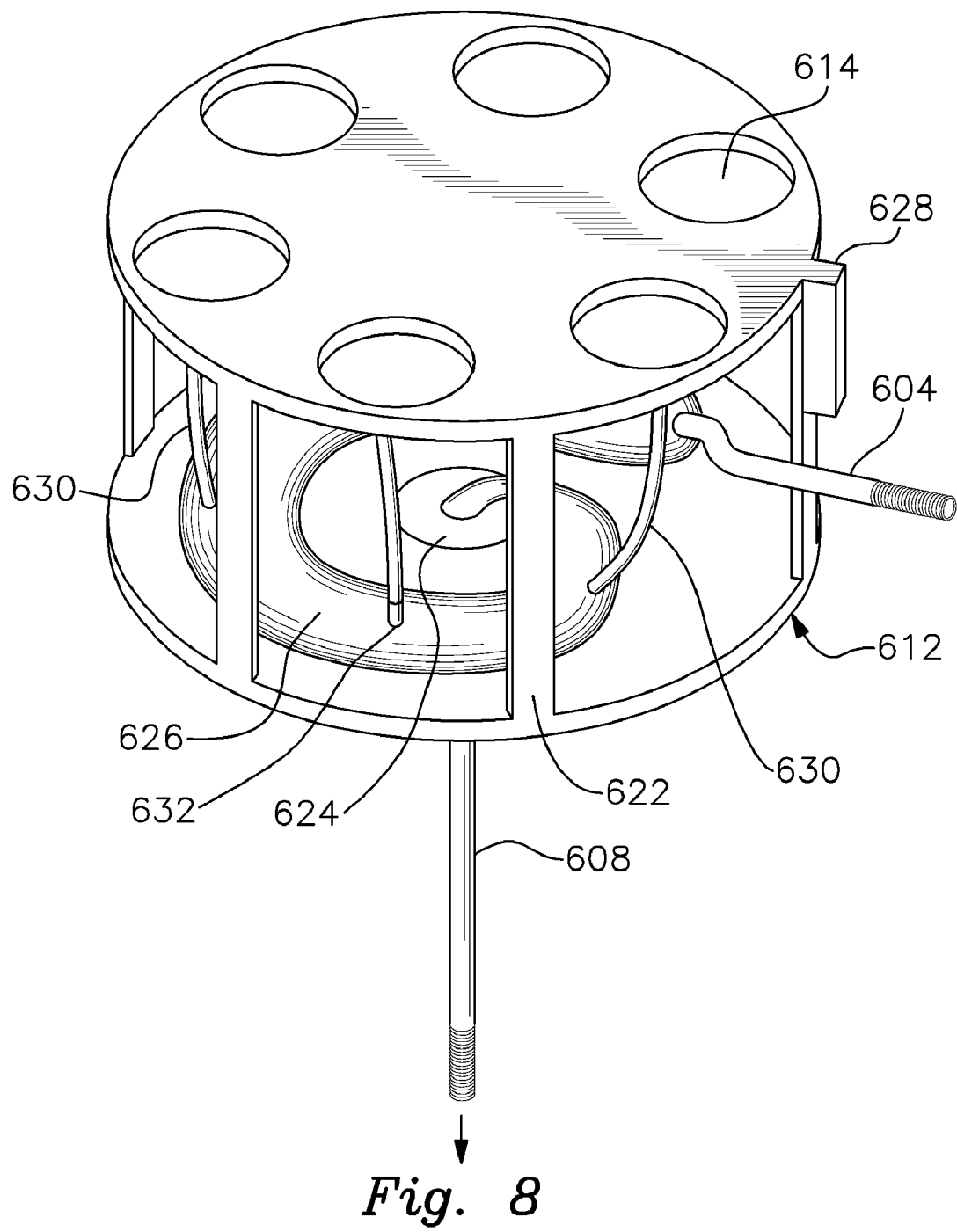
FIG. 8 shows a perspective view of an embodiment of a manifold cartridge assembly.

FIG. 8 is an illustration of one embodiment of a manifold cartridge assembly 612 removed from the manifold cap 602 (shown in FIG. 7). The structure of the manifold cartridge assembly 612 is supported by a frame 622. On the superior side of said frame is one or more septum 614. Typically, one septum 614 would be provided for each vessel 514 (shown on FIG. 5). Each vessel port 532 on the cartridge assembly 522 mates with the corresponding septum 614 on the manifold cartridge assembly 612 to form a pressure-resistant seal. In one embodiment the vessel port 532 is similar to a hypodermic needle and the septum 614 is a rubber-like material and when the vessel port 532 is mated with the septum 614 the hypodermic needle pierces the rubber-like material creating a pressure-resistant union. Other suitable means of connecting the cartridge assembly 522 to the manifold cartridge assembly 612 have been considered and may include, inter alia, clips, nipples, clamps and other connectors.

Still referring to FIG. 8, in this embodiment each septum 614 is integrally connected to a conduit 630 that conducts the fluid to a manifold chamber 626. The manifold chamber 626 is generally hollow and has a predetermined interior volume specific to the application. For example, in some applications it is preferable to avoid commingling of the various fluids as they are dispensed in succession and therefore a minimal volume is desired. In other applications a greater volume of the manifold chamber and/or an agitator inside the manifold chamber 626 may be desired to promote mixing of the fluids as the fluids are dispensed. Optionally, a valve 632 that prevents back-flow of fluid into the conduit 630 is inserted between all or each conduit 630 and the manifold chamber 626. A key 628 may be used to ensure consistent orientation of the manifold cartridge assembly 612 with the manifold cap 602 when engaged into key slot 610. A port 624 in the frame 622 provides an egress for the fluid port 608.

In the embodiment of the manifold cartridge assembly 612 demonstrated in FIG. 8 there is a fluid port 604 that receives fluid from a source external to the device and a fluid port 608 where any fluids finally exit the device. One of the contemplated applications that this embodiment of the manifold cartridge assembly would be well suited is for intra-venous injections. In this application it is possible that the fluids, in this example drugs, dispensed should not be mixed or commingle. To remedy this potential issue a sterile saline solution source can be connected to the fluid port 604. After or while one (or more) of the drugs is delivered from the vessel 514, through the vessel port 532, septum 614 and conduit 630 into the manifold chamber 626 the sterile saline solution is introduced through the fluid port 604 to flush the drug out of the manifold chamber 626 and through a fluid port 608 where the drug exits the device and is pushed toward a patient by the sterile saline flow. In a preferred embodiment there is a one-way valve between the septum 614 and conduit 630 to prevent any backflow into the vessel 514.

Figure 9:
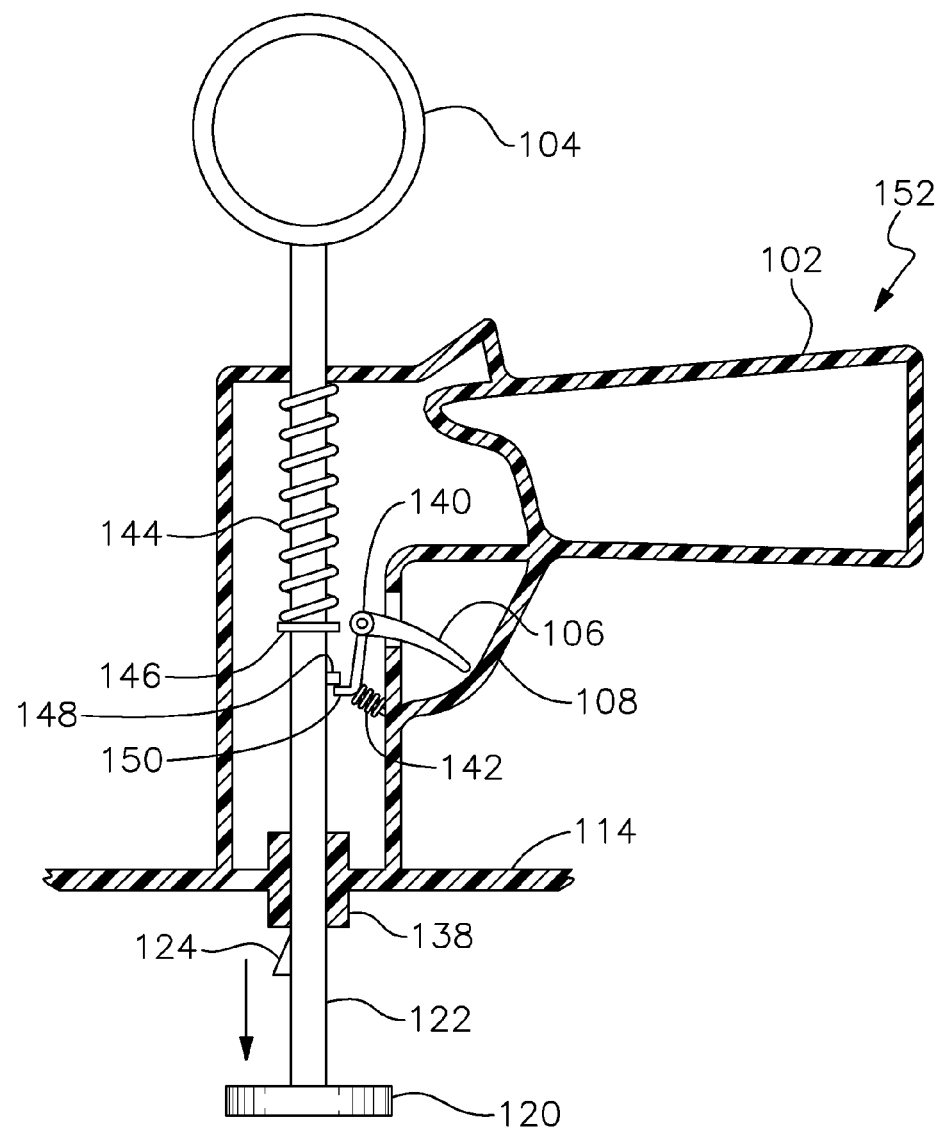
FIG. 9 is a representation of a cross-sectional view of an embodiment of a manual head assembly.

FIG. 9 is a cross-sectional view of the handle assembly 152 and shows an embodiment of the internal components of the manual head assembly 100. This embodiment comprises, inter alia, a handle 102, a cocking lever 104, a trigger 106, a trigger guard 108, a turntable 114, a plunger 120, a shaft 122, a stop 124, a guide 138, a fulcrum 140, a spring 142, a spring 144, a stop 146, a stop 148 and a catch 150. When preparing the device for use the user manually pulls on the cocking lever 104 to compress the spring 144 that is held in place on the shaft 122 by the stop 146. When the spring 144 is adequately compressed the catch 150 contacts the stop 148 to hold the spring 144 under compression. The catch 150 is biased toward and engages the stop 148 by means of a spring 142. When the user desires to dispense a fluid the trigger 106 is pulled and the trigger pivots at the fulcrum 140, compresses the spring 142 and the catch 150 clears the stop 148 freeing the spring 144 to push against the stop 146 and thereby push the shaft 122 and plunger 120. The force of the spring 144 is transferred to the piston 524 (shown in FIG. 5) to initiate dispensing a fluid contained in the vessel 514 (shown in FIG. 5). The shaft 122 maintains axial alignment by means of a guide 138. A trigger guard 108 is provided to prevent inadvertently pressing the trigger 106.

Figure 10:
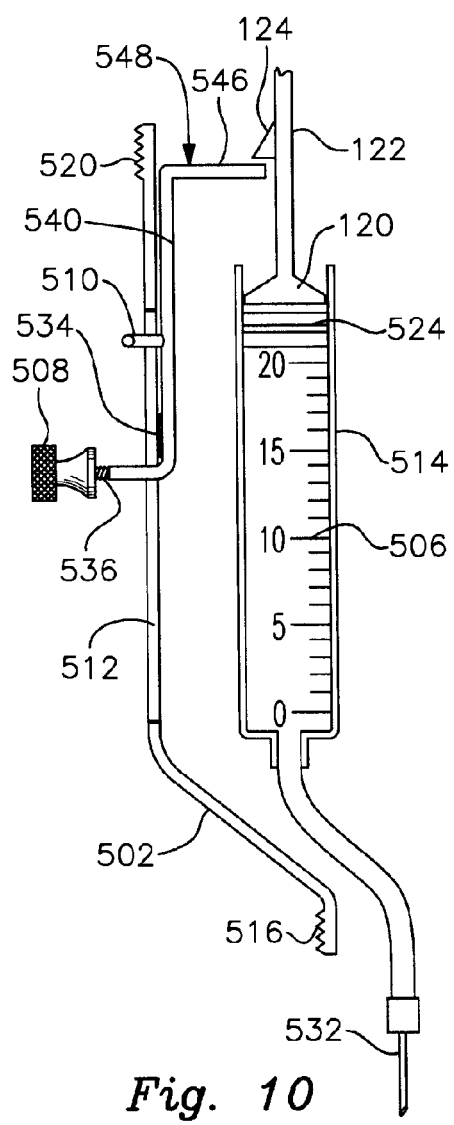
FIG. 10 is a partial cross-sectional view showing an embodiment of a case assembly.
Figure 11:
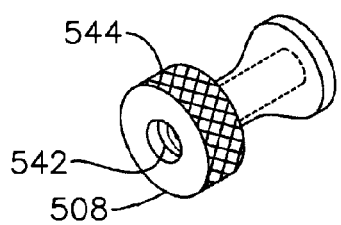
FIG. 11 shows a perspective view of an embodiment of a thumb lock.
Figure 12:
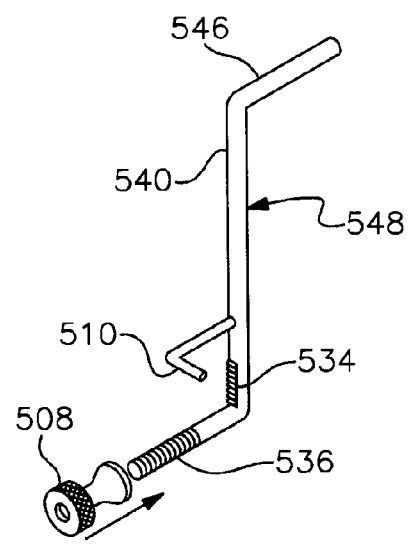
FIG. 12 is a perspective view of an embodiment of a thumb lock assembly.

FIGS. 10, 11 and 12 show in more detail one of the embodiments of the thumb lock assembly 548 that is utilized to limit the travel of the piston 524 effectively stopping the dispensing of fluid. In this embodiment of the device the thumb lock assembly comprises, inter alia, a rod 540, an indicator 510, a stop 546, teeth 534, thumb lock 508, threads 536 and threads 542. The indicator 510, thumb lock 508 and threads 536 are outside of the case 502 while the stop 546, rod 540 and teeth 534 are inside the case 502 for normal operation. The thumb lock 508 has internal threads 542 corresponding to threads 536 on the rod 540. When the thumb lock assembly 548 is locked the thumb lock 508 is threaded onto threads 536 and the thumb lock 508 contacts the exterior of the case 502 while the teeth 534 contact the interior of the case 502 with such firmness as to prevent movement of the thumb lock assembly 548 relative to the case 502. A knurled grip 544 on the thumb lock 508 may be provided to improve the users grip on the thumb lock 508. To adjust the thumb lock assembly 548 the thumb lock 508 is loosened and the thumb lock assembly 548 is freed to travel along the guide 512, also shown in FIG. 4. The indicator 510 can be viewed by the user on the exterior of the case 502 adjacent to the viewing port 504. When the thumb lock assembly 548 is locked and the plunger 120 is in motion dispensing fluid and the piston 524 has traveled to the point indicated by the indicator 510 the stop 124 on the shaft 122 contacts the stop 546 on the thumb lock assembly 548 preventing the shaft 122 and plunger 120 from traveling further thus stopping dispensing more fluid. The dimensions of the thumb lock assembly 548 are such that when the indicator 510 is adjacent to the graduations 506 seen through the viewing port 504 the piston 524 will not travel further than the indicated level inside the vessel 514.

Figure 13:
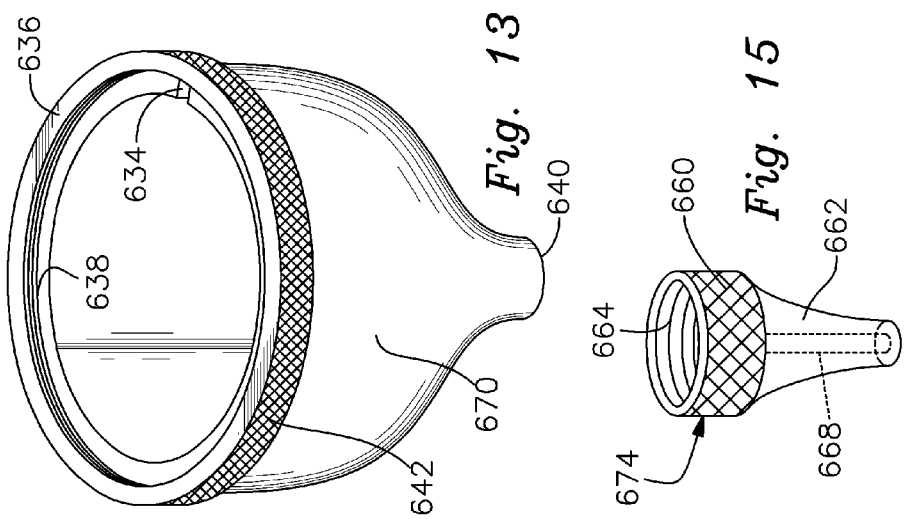
FIG. 13 is a representation of a perspective view of an embodiment of a manifold cap.

FIG. 13 shows another alternative embodiment of a manifold cap 670 with features that are comprised of, inter alia, a key slot 634, a seat 636, threads 638, a knurled grip 642 and a port 640. This embodiment is attached to the case assembly 500 by means of threads 638 screwed onto threads 516 with the assistance of the knurled grip 642 until the seat 636 contacts the case 502. As alternatives to the threads 638 the manifold cap 670 could be attached to the case 502 by many commonly available means such as clips, welds, adhesives, brackets or other means. A key slot 634 ensures proper alignment of the manifold cap 670 relative to a manifold cartridge assembly 672 (shown in FIG. 14).

Figure 14:
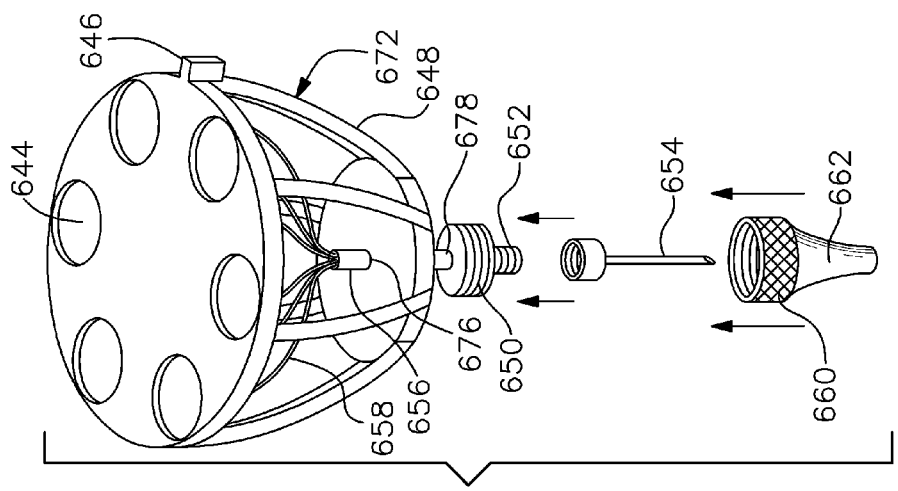
FIG. 14 shows an exploded perspective view of an embodiment of a manifold cartridge assembly.
Figure 15:
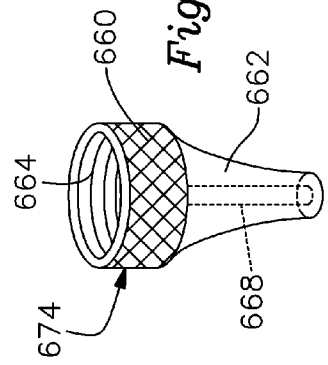
FIG. 15 is a perspective view of an embodiment of a guide assembly.

FIGS. 14 and 15 depict an embodiment of a manifold cartridge assembly 672 removed from the manifold cap 670. The manifold cartridge assembly 672 is generally supported by a frame 648. On a superior side of said frame 648 is one or more septum 644. Typically, one septum 644 would be provided for each vessel 514 (shown on FIG. 5). Each vessel port 532 on the cartridge assembly 522 mates with the corresponding septum 644 on the manifold cartridge assembly 672 to form a pressure-resistant seal. In a preferred embodiment there is a one-way valve between the vessel 514 and the manifold cartridge assembly 672 to prevent backflow into the vessel 514. In one embodiment the vessel port 532 is similar to a hypodermic needle and the septum 644 is a rubber-like material and when the vessel port 532 is mated with the septum 644 the hypodermic needle pierces the rubber-like material creating a pressure-resistant union. Other suitable means of connecting the cartridge assembly 522 to the manifold cartridge assembly 672 have been considered and may include, inter alia, clips, nipples, clamps and other connectors.

Still referring to FIGS. 14 and 15, in this embodiment each septum 644 is integrally connected to a conduit 658 that conducts the fluid to a manifold chamber 656. The manifold chamber 656 is generally hollow and has a predetermined interior volume specific to the application. For example, in some applications it is preferable to avoid commingling of the various fluids as they are dispensed in succession and therefore a minimal volume is desired. In other applications a greater volume of the manifold chamber and/or an agitator inside the manifold chamber 656 may be desired to promote mixing of the fluids as the fluids are dispensed. Optionally, a valve that prevents back-flow of fluid into the conduit 658 is inserted between all or each conduit 658 and the manifold chamber 656. A key 646 may be used to ensure consistent orientation of the manifold cartridge assembly 672 with the manifold cap 670 when the key 646 is engaged into key slot 634. A port 676 in the frame 648 provides an egress for a conduit 678. On said conduit 678 are threads 652 and threads 650. Threads 652 extend below and have a smaller diameter than the threads 650. A needle 654 or other delivery device is threaded onto the threads 652 on the conduit 678. A guide assembly 674 comprised of, inter alia, a knurled grip 660, a guide 662, threads 664 and a shaft 668 is placed over the needle 654 and threaded via threads 664 onto threads 650. The guide assembly 674 can be threaded onto threads 650 to varying depths thus exposing more or less of the tip of the needle 654. This feature controls the precise depth that the needle 654 can penetrate, for example into the patient.

One of the contemplated applications that this embodiment of the manifold cartridge assembly would be well suited for is for intra-dermal or intramuscular injections. In this application it is not typically suitable to utilize a flushing saline solution as described above for the manifold cartridge assembly 612 shown in FIG. 8 because too great a volume of fluid would be dispensed under the skin or into the muscles of the patient. In this embodiment of the manifold cartridge assembly 672 it may be preferred to have minimum interior volume of the manifold chamber 656.

Figure 16:
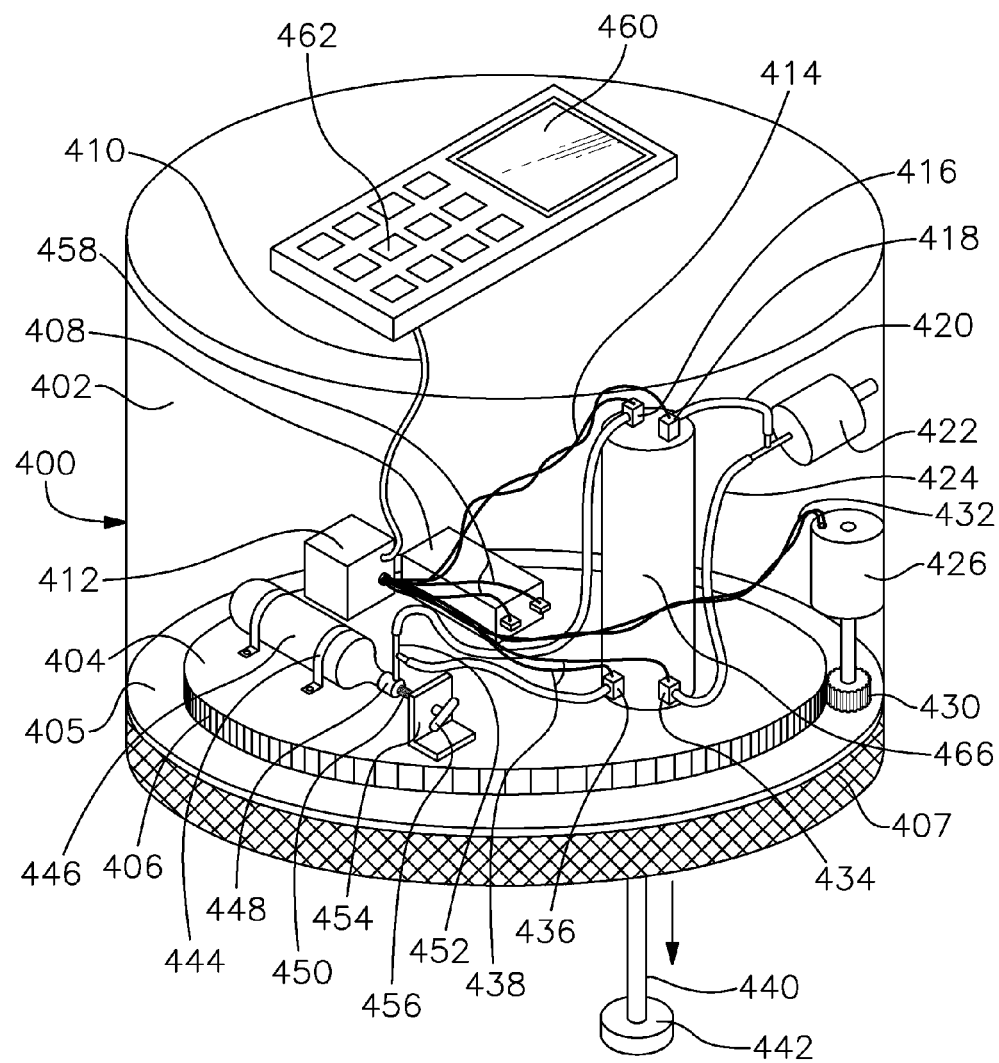
FIG. 16 is a representation of a perspective view of an embodiment of a pneumatic powered head assembly.

Now referring to FIG. 16 where an embodiment of a pneumatic head assembly 400 is shown. The pneumatic head assembly is housed in a case 402 made of a durable material to provide structure and protection for the contents of the case 402. A base 405 is affixed to the bottom side of the case 402. A threaded ring 407 with knurled edges is at the base of the case 402 and is used to thread the pneumatic head assembly 400 to the case assembly 500 at threads 520 (shown in FIG. 3). A turntable 404 is in the interior of the case 402 and is rotatable relative to the base 405. The turntable 404 has a plurality of teeth 406 around its periphery. The force for rotating the turntable 404 is provided by a motor 426 connected to a gear 430. The gear 430 engages the teeth 406 thereby transferring the force of the motor 426 to cause a rotation of the turntable 404 relative to the base 405. A variety of types of gears have been contemplated that would be equally effective alternative for gear 430 that include, inter alia, a worm-type gear if the axis of the motor 426 is perpendicular to the axis of the turntable 404 or a traditional circular gear if the axis of the motor 426 is parallel to the axis of the turntable 404. The motor 426 is connected to the CPU 412 (central processing unit) by a cable 432. In the preferred embodiment of the pneumatic head assembly 400 the motor 426 is a stepping motor.

The motor 426 and the rest of the pneumatic head assembly 400 can be controlled by a CPU 412 that is powered by a battery 408 or other power source such as regular alternating current, photo-voltaic cells, fuel cells or any other available power source. The battery 408 is connected to the CPU 412 by wires 458. The CPU 412 receives input from an input device 462 that may be comprised of, for example, a keypad, buttons, knobs, dials or any other input means. The CPU 412 is connected to the input device 462 by a cable 410.

Optionally, the CPU 412 may also utilize a display 460 to show the user relevant information as to the operation of the device. For example, the display 460 could show the user a variety of menus to aid in programming the CPU 412 for a particular purpose, such as the status of the device, time, pressure, volume of fluid remaining or dispensed by the device, battery power, identification of fluid or any of a wide variety of information relevant to the user of the device. The CPU 412 is connected to the display 460 by a cable 410 or other means.

The CPU 412 may also control, inter alia, a valve 416, a valve 418, a valve 434 and a valve 436 each mounted onto a cylinder 466. Valve 416 and valve 418 are connected to the CPU 412 by a cable 414. Valve 434 and valve 436 are connected to and controlled by the CPU 412 through cable 438. Valve 416, valve 418, valve 434 and valve 436 control pressurized fluid passing into and out of the interior of the cylinder 466.

In one of the preferred embodiments of the pneumatic head assembly 400 a pressure vessel 446 is secured by a mount 444 onto the turntable 404. The pressure vessel 446 is connected to a receiver 448 and held into place by a tap 450 that is in turn secured by a mount 454. A handle 456 aids the user in securing the tap 450 to the pressure vessel 446 creating a pressure resistant seal. A conduit 452 carries fluid under pressure to valve 416 and valve 436. A conduit 420 is connected to valve 418 and provides a pathway for exhaust to escape out of the cylinder 466 and exit the device through a muffler 422. A conduit 424 is connected to valve 434 and provides a pathway for exhaust to escape out of the cylinder 466 and exit the device through the muffler 422. In the preferred embodiment the pressure vessel 446 is a common carbon dioxide cartridge such as are commonly used in pellet guns.

Still referring to FIG. 16, an alternate embodiment of the pneumatic head assembly 400 consists of, inter alia, substituting a hydraulic pump (not depicted) instead of the pressure vessel 446. The hydraulic pump is controlled by CPU 412 and powered by a battery 408. Conduit 452 carries hydraulic fluid to valve 416 and valve 436.

Figure 17:
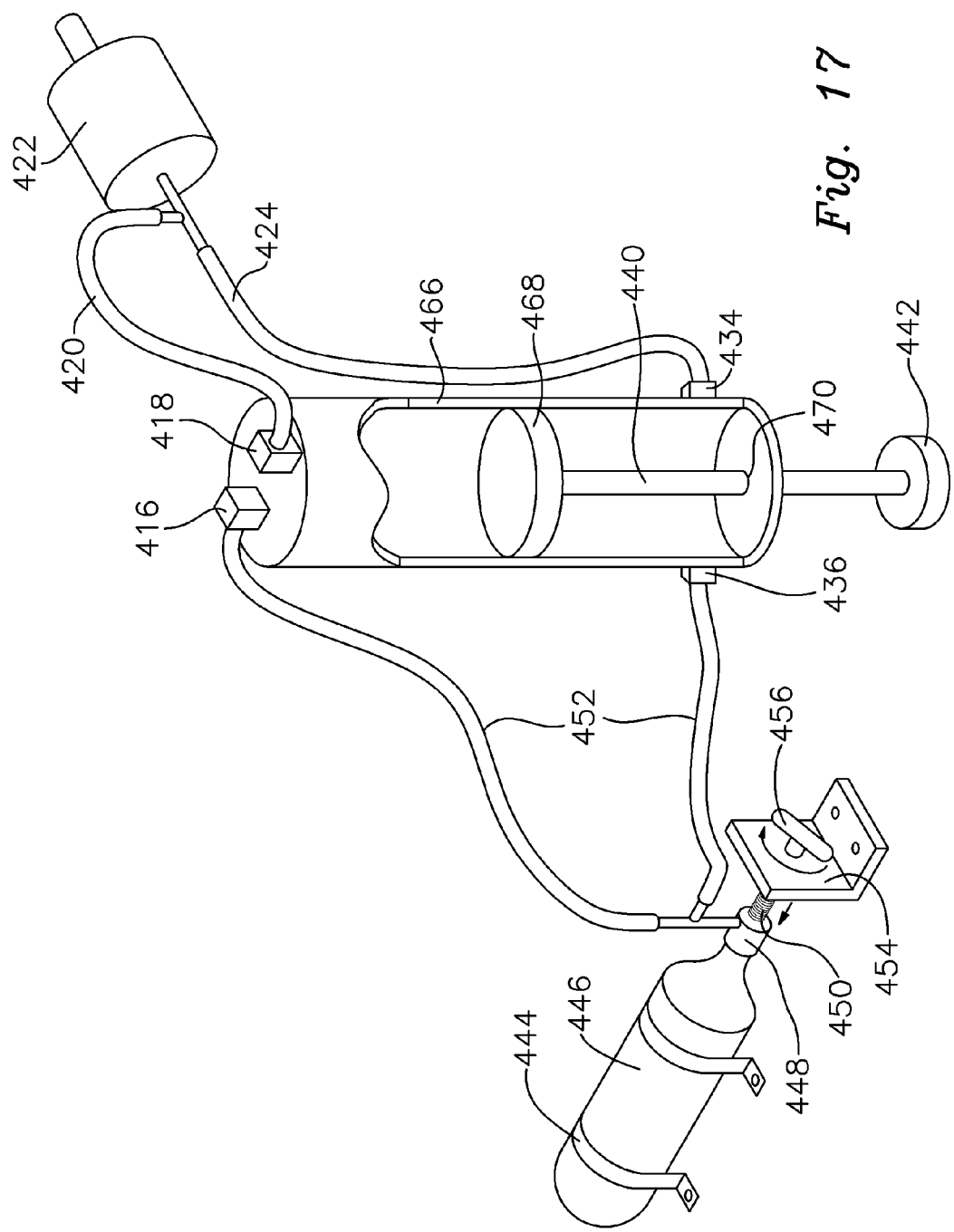
FIG. 17 shows a perspective view of a partial cross-section of an embodiment of a pneumatic head assembly.

Now referring to FIG. 17 where a partial cutaway view of an embodiment of the pneumatic head assembly 400 (as shown in FIG. 16) showing a cross section of said cylinder 466. Said pressure vessel 446 is mounted securely by said mount 444 to said turntable 404. Said tap 450 is secured to the turntable 404 by mount 454. Said conduit 452 is secured to the pressure vessel 446 at the receiver 448 to form a pressure resistant seal by tightening the handle 456 thereby securing the union between the receiver 448 and the pressure vessel 446.

Still referring to FIG. 17, on the interior of the cylinder 466 is a piston 468 connected to a shaft 440 that passes though the floor of the cylinder 466 at a seal 470 and terminates in a plunger 442 that retractably extends through and below said turntable 404. To move the plunger 442 down, the valve 416 is opened and valve 418 is closed thereby permitting the fluid in the pressure vessel 446 to flow through the conduit 452 into the cylinder 466 creating high pressure above the piston 468 while at the same time valve 436 is closed and valve 434 opens so that the volume inside the cylinder 466 below the piston 468 is open to ambient pressure through the conduit 424 and muffler 422. To raise the plunger 442 the inverse must occur: the valve 436 is opened and valve 434 is closed thereby permitting the fluid in the pressure vessel 446 to flow through the conduit 452 into the cylinder 466 creating high pressure below the piston 468 at the same time valve 416 is closed and valve 418 opens the volume inside the cylinder 466 above the piston 468 to ambient pressure through the conduit 420 and muffler 422.

Returning now to FIG. 16 this embodiment of a pneumatic head assembly 400 is typically used in conjunction with a case assembly 500 as shown in FIG. 3 and a manifold assembly 600 as shown in FIG. 6. Both the pneumatic head assembly 400 and manifold assembly 600 are connected to the respective ends of the case assembly 500 to form a single unit. When the device is used the plunger 442 comes into contact with the piston 524 on the top of the vessel 514 and pushes any fluid contained in the vessel 514 out of the device through the manifold assembly 600.

Figure 18:
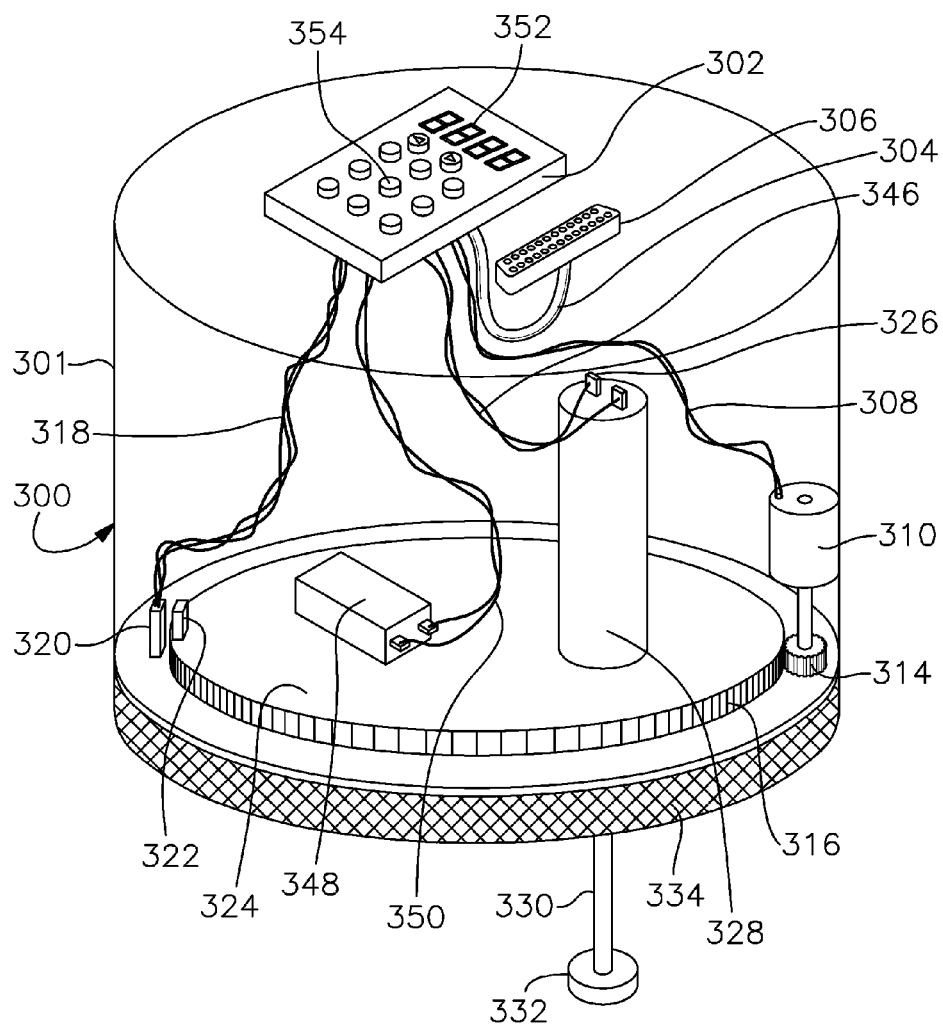
FIG. 18 illustrates a perspective view of an embodiment of an electronic head assembly.

Now referring to FIG. 18 where an embodiment of an electronic head assembly 300 is shown. The structure of the electronic head assembly 300 is provided by a case 301. At the base of said case 301 is a threaded ring 334 that is used to connect the electronic head assembly 300 to a case assembly 500 at threads 520 (shown on FIG. 3). The electronic head assembly 300 is controlled by a central processing unit (CPU) 302 and powered by a battery 348 and connected to said battery 348 by a cable 350. The CPU 302 has an input device 354 that serves as an interface between the user and the invention. The input device 354 may consist of, inter alia, a keypad, dials, buttons or other similar means. The CPU 302 is also connected to a display 352 such as a liquid crystal display (LCD), light emitting diodes (LED) or other suitable means of display that are commonly used. The display 352 shows information to the user such as status, programs, power supply, fluid dispensed or remaining and any other relevant information. A socket 306 is optionally present and provides a means to connect a computer device to control, program or monitor said CPU 302. Said socket 306 is connected to said CPU 302 by a cable 304

Said CPU 302 is connected to a motor 310 by a cable 308. Said motor 310 is connected to a gear 314 that interfaces with teeth 316 around the circumference of a turntable 324. Said CPU 302 controls and activates said motor 310 that in turn rotates said gear 314 that in turn rotates said turntable 324 about its axis. In the preferred embodiment said motor 310 is a stepping motor.

Still referring to FIG. 18, in a preferred embodiment a lineal actuator 328 is fixed onto said turntable 324. Said lineal actuator 328 extends and retracts a shaft 330 that terminates in plunger 332 extendable below said turntable 324. Said lineal actuator 328 is controlled by said CPU 302 and is connected to said CPU 302 by cable 346 connected to terminals 326 on the lineal actuator 328.

Figure 19:
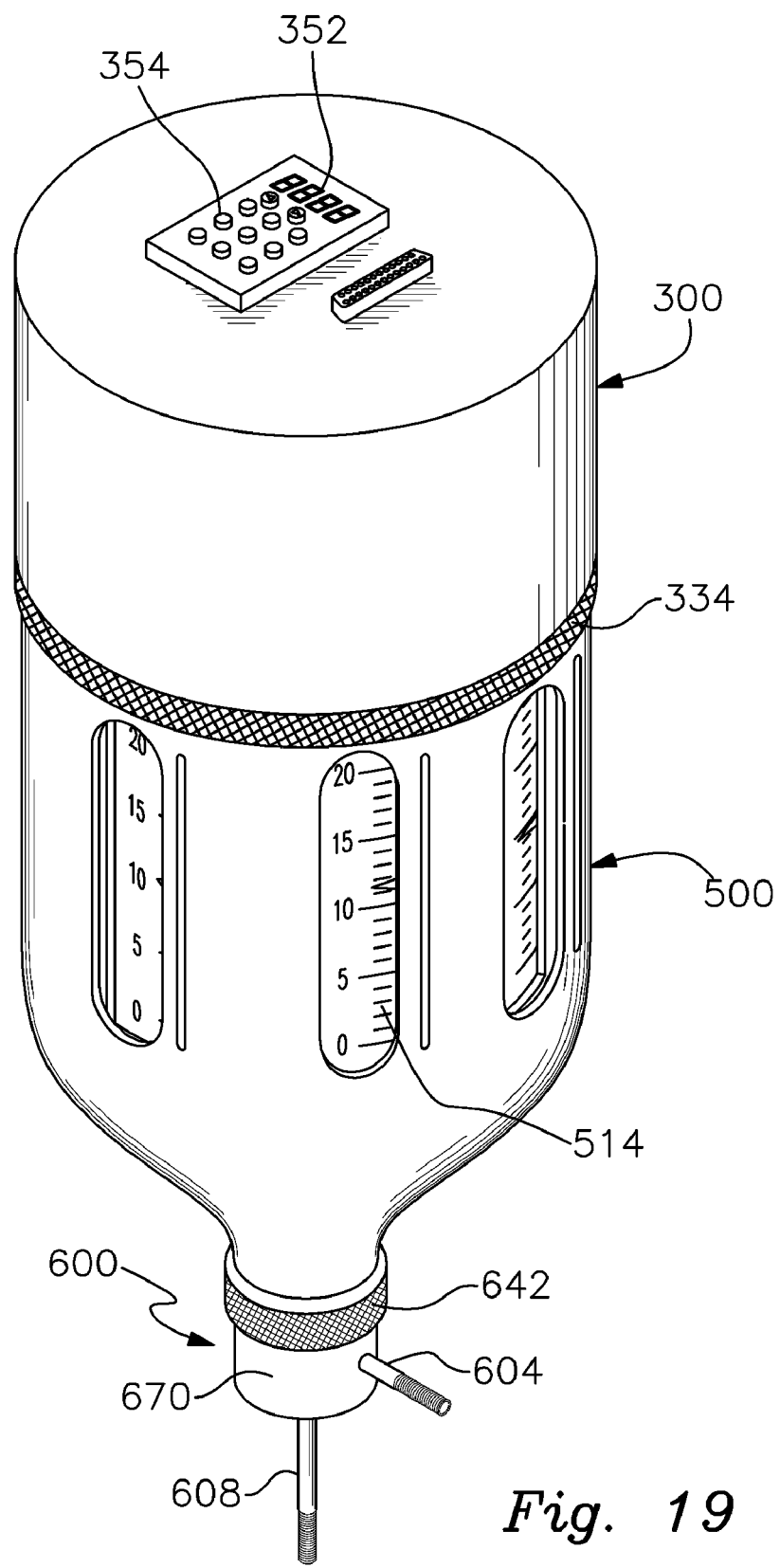
FIG. 19 shows a perspective view of an embodiment of the invention with an electronic head assembly.

Yet referring to FIG. 18, a sensor 320 is connected to said CPU 302 by a cable 318. Said sensor 320 is fixed relative to the case 301. A marker 322 is fixed onto the turntable 324. When said turntable 324 rotates the marker 322 past the sensor 320 an input into the CPU 302 is generated to calibrate the precise angular position of the turntable 324, and therefore necessarily the lineal actuator 328, relative to the case 301. The sensor 320 ensures that the plunger 332 is oriented directly over the proper vessel 514 (shown in FIG. 3) when the electronic head assembly 300 is attached to the case assembly 500 as shown in FIG. 19. The preferred embodiment of the sensor 320 is a Hall Effect Sensor with a magnet as the marker 322, but other sensors, such as a contact switch, would be equally effective.

FIG. 19 shows the assembled invention with the electronic head assembly 300. When the invention is in use the electronic head assembly 300 is secured to a case assembly 500 that is in turn connected to a manifold assembly 600. The manifold assembly as shown in FIGS. 13, 14 and 15 may be substituted for the manifold assembly 600 when it is suitable to the application of the invention, for example when the invention is used to administer intra-muscular or intra-dermal injections.

Figure 20:
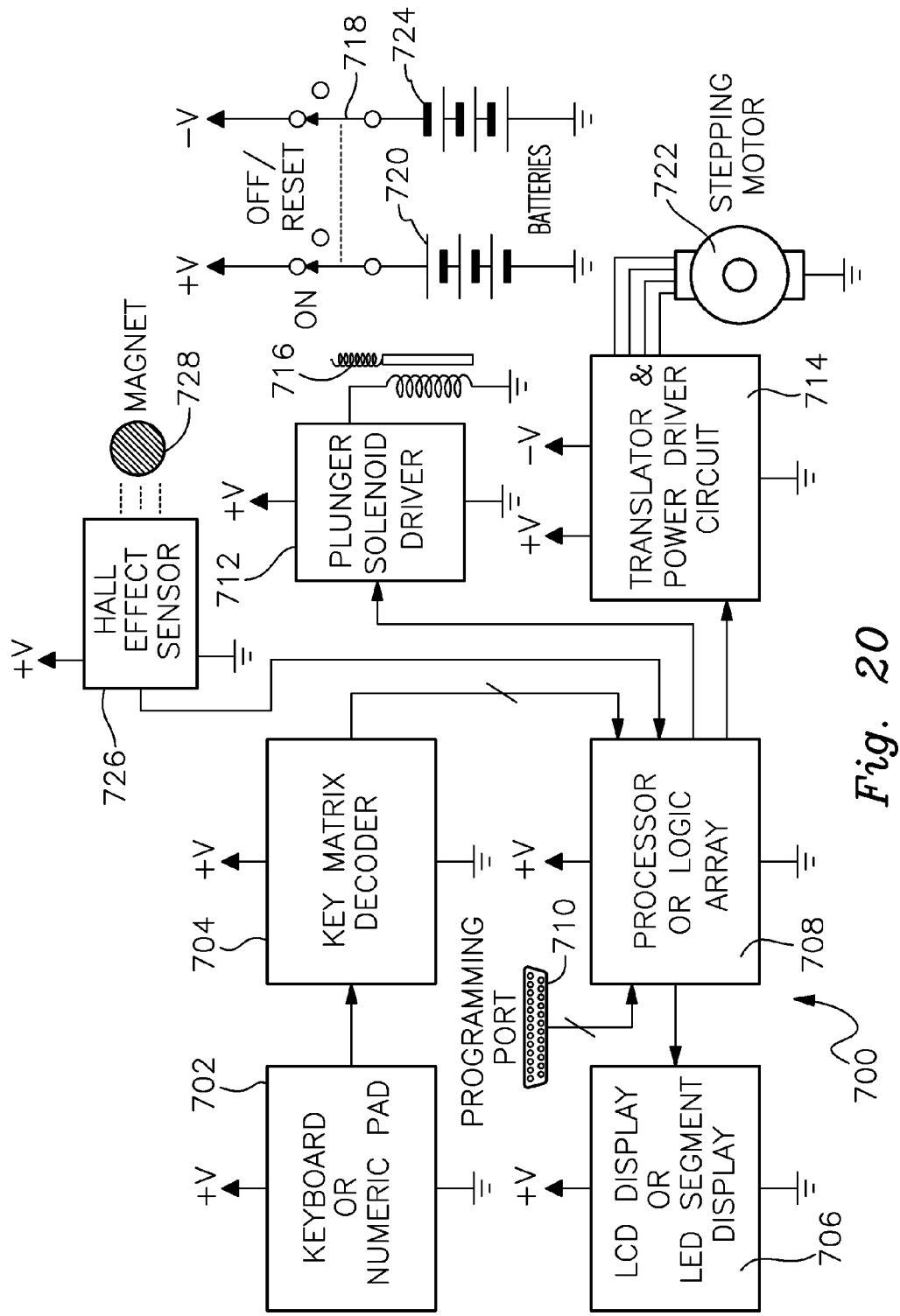
FIG. 20 is an example of a circuit diagram of an electrical head assembly.

FIG. 20 shows an example of a circuit configuration 700 utilized with, and contained inside, the electronic head assembly 300 as shown in FIG. 18. A processor 708 is the main controller and may also comprise a logic array and is powered by a battery 720. The circuit configuration 700 is powered up by switch 718. An input device 702 feeds user input through a decoder 704 into the processor 708. In the preferred embodiment the input device 702 may be, for example, a keyboard, numeric pad, buttons, switches or other commonly used input devices.

Said processor 708 optionally may also be connected to a port 710 to connect the circuit configuration 700 to an external computer that may perform such functions as programming, monitoring and/or controlling the circuit configuration 700.

A display 706 is optionally connected to the processor 708 to show information to the user such as the device status, fluid to be dispensed, fluid remaining, programming sequence, battery supply or any other relevant information.

Still referring to FIG. 20, a sensor 726 and marker 728 also provide an input into the processor 708 to aid in calibration of the position a lineal actuator 716 relative to the dispensed vessel 514 as described above in the discussion on FIG. 18 where sensor 320 is analogous to sensor 726, marker 322 is analogous to marker 728 and lineal actuator 328 is analogous to lineal actuator 716. In the preferred embodiment the sensor 726 is a Hall Effect Sensor that produces a signal when a magnet, shown as marker 728, passes next to the sensor 726. As an alternative, the sensor 726 may be a contact switch or other suitable means to indicate to the processor 708 when the sensor 726 is positioned next to the marker 728.

Said processor 708 gives input to a driver 714 that in turn activates a motor 722. In the preferred embodiment the motor 722 is a stepping motor. Said motor 722 is analogous to the motor 310 in FIG. 18 and performs to rotate the turntable 324 relative to the case 301, also shown in FIG. 18. In the preferred embodiment the driver 714 is a translator and power driver circuit. The driver 714 is connected to battery 720 with a positive potential to turn the motor in one direction and also connected to battery 724 with a negative potential to turn the motor 722 in the opposite direction.

Said processor 708 also controls a driver 712 that in turn activates a lineal actuator 716 as also shown in FIG. 18 as the lineal actuator 328. As described in the discussion on FIG. 18, above, the lineal actuator 716 provides the force to dispense fluid contained in a vessel 514, as shown in FIG. 3, when the shaft 330 and plunger 332, as shown in FIG. 18, extend and press upon the piston 524, as shown in FIG. 3.

Figure 21:
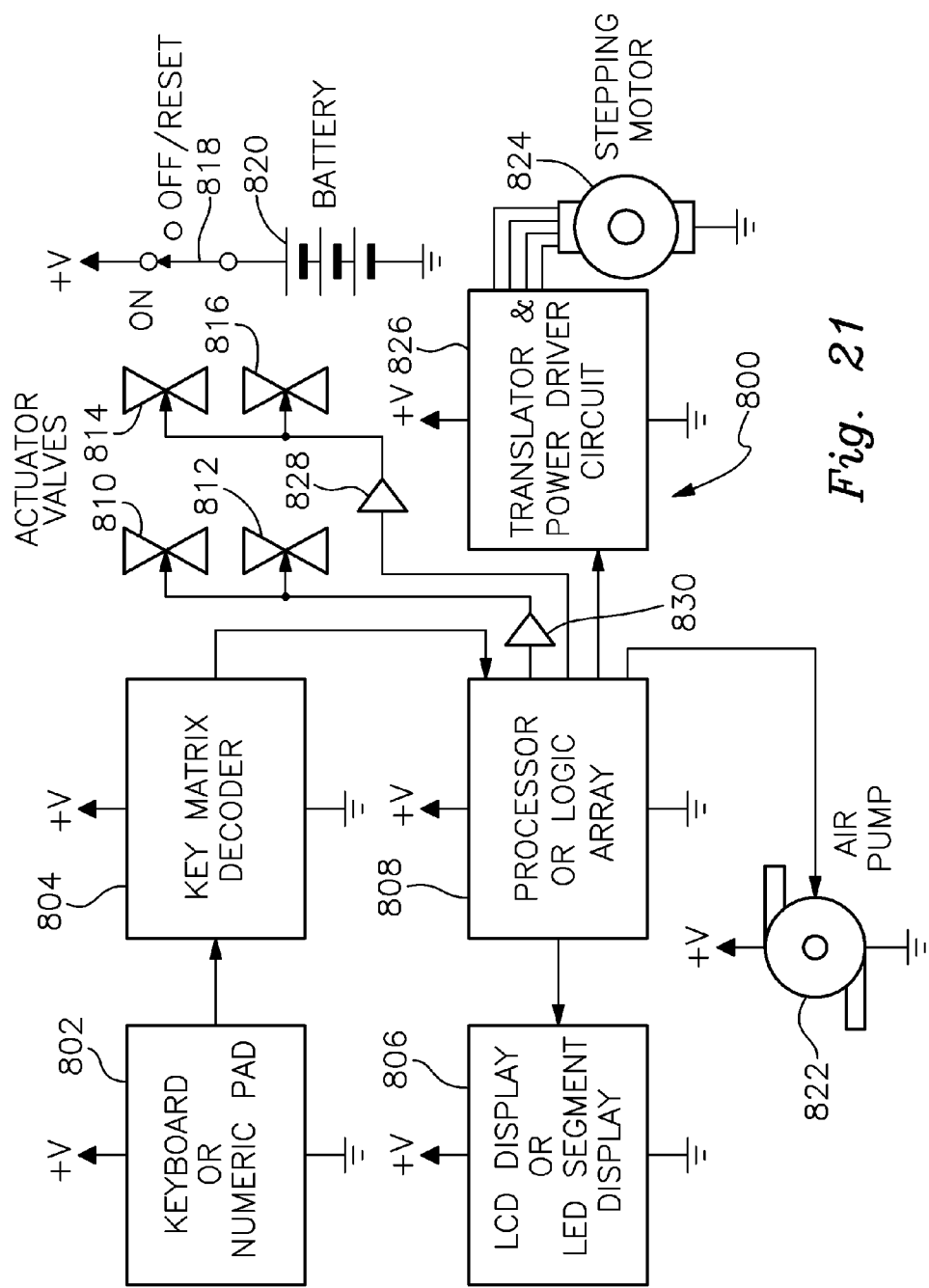
FIG. 21 is an example of a circuit diagram of a pneumatic head assembly.

Now referring to FIG. 21 that shows a circuit configuration 800 for the pneumatic head assembly 400, as shown in FIG. 16 and described above. Said circuit configuration 800 is typically contained inside the pneumatic head assembly 400 as shown in FIG. 16. A processor 808 is the main controller and may also comprise a logic array and is powered by a battery 820. The circuit configuration 800 is powered up by switch 818. An input device 802 feeds user input through a decoder 804 into the processor 808. In the preferred embodiment the input device 802 may be, for example, a keyboard, numeric pad, buttons, switches or other commonly used input devices.

Said processor 808 optionally may also be connected to a port (not depicted) to connect the circuit configuration 800 to an external computer that may perform such functions as programming, monitoring and/or controlling the circuit configuration 800, similar to port 710 described in the discussion of FIG. 20, above.

A display 806 is optionally connected to the processor 808 to show information to the user such as the device status, fluid to be dispensed, fluid remaining, programming sequence, battery supply or any other relevant information.

Still referring to FIG. 21, a sensor and marker (neither depicted in FIG. 21) similar to the sensor 320 and marker 322 shown on the electronic head assembly 300 as shown in FIG. 18 and described above may also be present to aid in calibration of the invention. In the preferred embodiment the sensor 320 is a Hall Effect Sensor that produces a signal when a magnet, shown as marker 322, passes next to the sensor 320. As an alternative, the sensor 320 may be a contact switch or other suitable means to indicate to the processor 808 when the sensor 320 is positioned next to the marker 322.

Said processor 808 gives input to a driver 826 that in turn activates a motor 824. In the preferred embodiment the motor 824 is a stepping motor. Said motor 824 is analogous to the motor 426 in FIG. 16 and performs to rotate the turntable 404 relative to the case 402, also shown in FIG. 16. In the preferred embodiment the driver 826 is a translator and power driver circuit. The driver 826 is connected to battery 820.

Said processor 708 also controls a driver 828 and a driver 830. Said driver 828 operates to either close or open both a valve 814 and a valve 816 simultaneously. Said valve 814 and said valve 816 are analogous to valve 416 and valve 434, respectively, shown in FIG. 17. Said driver 830 operates to close or open both a valve 810 and a valve 812 simultaneously. Said valve 810 and valve 812 are analogous to valve 418 and valve 436, respectively, shown in FIG. 17. Valve 810, valve 812, valve 814 and valve 816 operate in concert as described for the respective valves as shown in FIG. 17 and described above in the discussion on FIG. 17 to move said piston 468, shaft 440 and plunger 442 up and down.

Said circuit configuration 800 includes a pump 822 to supply a pressure source as an alternative to the pressure vessel 446 as shown in FIG. 17. The pump 822 supplies a pressure greater than ambient pressure to valve 814 and valve 812.

Figure 22:
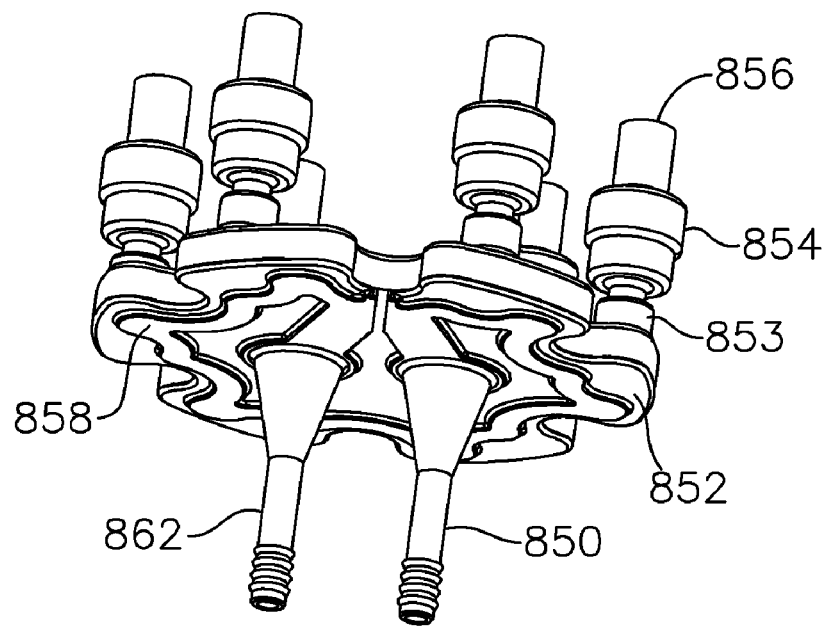
FIG. 22 is a perspective view of a manifold assembly.
Figure 23:
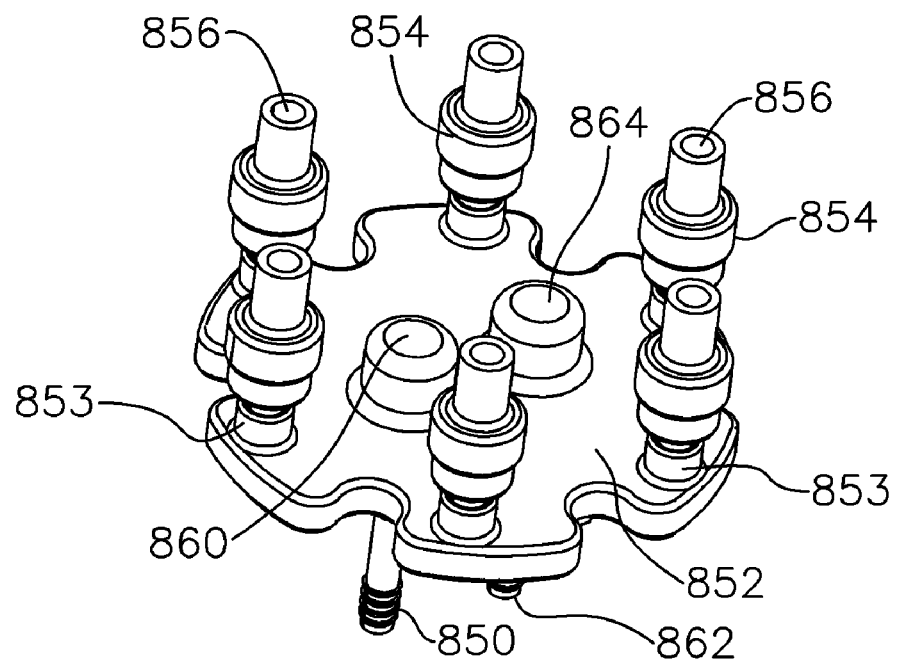
FIG. 23 is a perspective view of the manifold assembly shown in FIG. 22.

Now referring to FIG. 22 and FIG. 23 where the same manifold assembly is shown from differing perspective views. Said manifold assembly is comprised of, inter alia, a body 852, port 853, port 850, port 862, channel 858, valve 854, trap 864, trap 860 and receiver 856. Said valve 854 is connected to the body 852 by said port 853 and terminates in a receiver 856 that is dimensioned to connect to a cartridge assembly such as cartridge assembly 1200 shown in FIG. 25 and described in more detail below. The interior of said body 852 has a channel 858. Said channel 858 having a port 862 at one end and a port 850 at the other end. Said channel 858 is also open between port 862 and port 850 to the port 853. In the preferred embodiment there are multiple ports 853, valves 854 and receivers 856 affixed to the body 852 and having an opening into the channel 858. Said traps 860 and 864 are positioned between ports 850 and 862, respectively, and said channel 858 and, inter alia, serve to trap any gas bubbles that may pass through said chambers 850 and 864.

In the preferred method of medical use of the manifold assembly shown in the preceding figures a saline solution drip is first established to flow from a common saline solution bag, into port 850 and through the channel 858 past each port 853 then exiting the manifold assembly through port 862 then on to the patient. Drugs or other chemicals are introduced into the channel 858 through port 853 and are flushed out of the manifold assembly to the patient in the saline flow. Preferably, valves 854 are one way valves that prevent any flow into the valve 854 from the channel 858.

Figure 24:
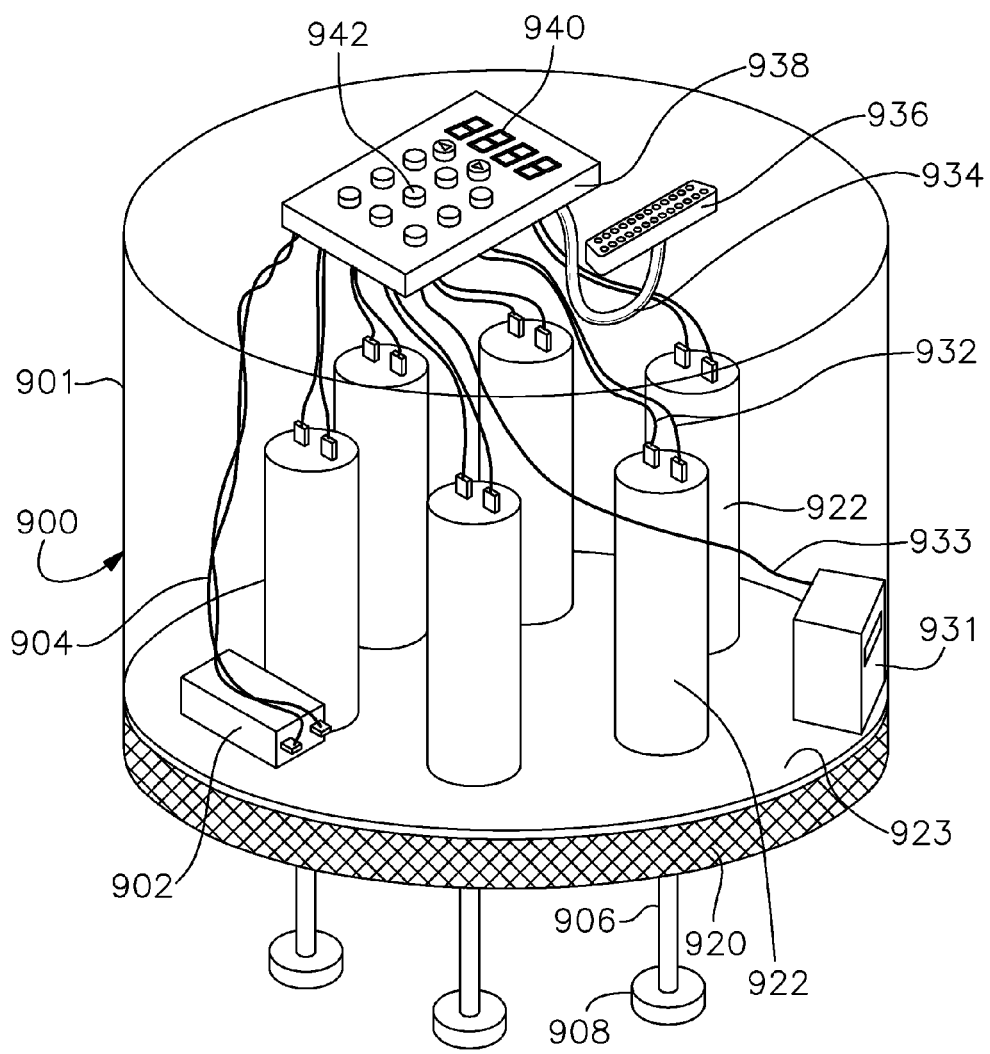
FIG. 24 is a perspective view of an embodiment of an electronic head assembly.

FIG. 24 shows a perspective view of an alternate embodiment of an electronic head assembly 900 comprising, inter alia, a case 901, battery 902, cable 904, head 908, shaft 906, grip 920, lineal actuators 922, a base 923, an output device 931, a cable 933, a cable 932, a cable 934, a port 936, a processor 938, a display 940 and an input device 942.

The structure of the electronic head assembly 900 is generally supported by the base 923 and the case 901. On said base 923 are mounted a plurality of lineal actuators 922. Movably extendable from the bottom of each one of said lineal actuators 922 is a shaft 906 that terminates on its lower end in a head 908.

In the preferred method of use this electronic head assembly 900 is attached to a case assembly such as the case assembly 500 as shown generally in FIG. 3. A grip 920 surface aids in the assembly and disassembly of the device. Each lineal actuator 922 is positioned directly over a piston 524. When said lineal actuator 922 is extended it presses on said piston 524 resulting in the dispensation of the contents of the vessel 514.

Said processor 938 is the primary controller of this electronic head assembly 900 and is powered by a battery 902 via cable 904. Said processor 938 has an input device 942 such as buttons, dials, a keypad or other similar means and a display 940 to show the user relevant information about the device. The processor optionally may be connected to a port 936 by a cable 934 to provide connectivity of the electronic head assembly 900 with an external device such as a computer, monitoring device, programmer, recorder, auxiliary display or other electronic accessory. Said processor 938 controls each of the lineal actuators 922 via cables 932. An output device 931 such as, for example, a printer may optionally be present and connects to the processor 938 by a cable 933.

Figure 25:
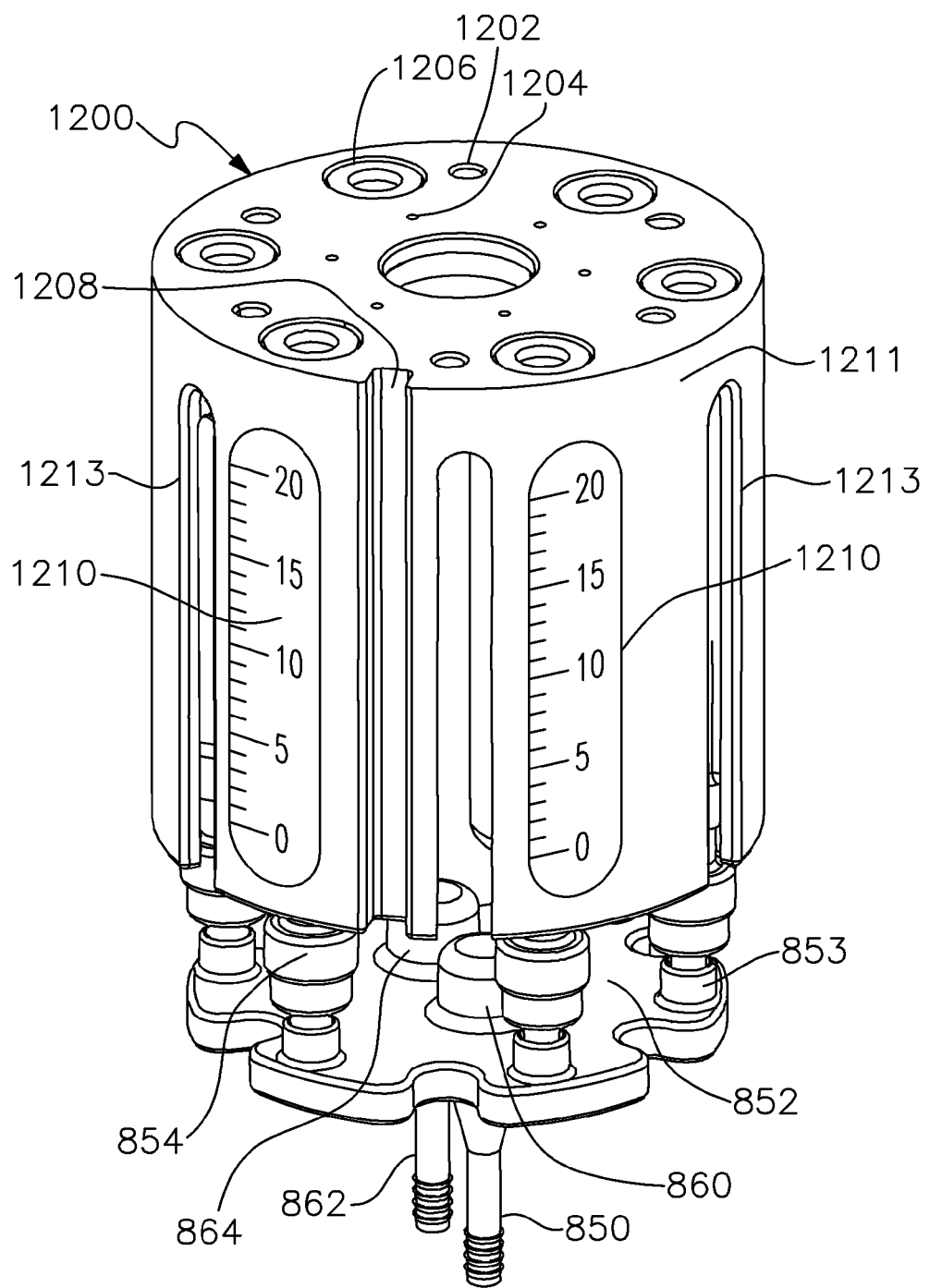
FIG. 25 is a perspective view of a cartridge assembly.

Now referring to FIG. 25 where a cartridge assembly 1200 is shown that comprises, inter alia, the manifold assembly shown in FIGS. 22 and 23, described above, a frame 1211, divots 1204, guides 1202, pistons 1206, a key slot 1208, slot 1213 and windows 1210. In the preferred embodiment said frame 1211 is a unitary piece that incorporates vessels that contain, for example, drugs. The vessels are sealed on top by said pistons 1206 and the contents of the vessels can be seen through said windows 1210. Said windows 1210 optimally have graduations to aid the user measure the volume of the contents of the vessel. The cartridge assembly 1200 can made of a translucent material so that the vessels can be viewed without the need for a distinct window. The key slot 1208 ensures that the cartridge assembly 1200 is fit into a case assembly, for example the case assembly shown generally in FIG. 4, at the proper orientation.

Said divots 1204 interact with a head assembly, such as the head assembly shown generally in FIG. 26 and described below, to aid in aligning the head with the cartridge assembly 1200. Said guide 1202 and said slot 1213 on the cartridge assembly 1200 are used with the stop assembly 1300, described below in the discussion on FIGS. 27 through 29.

In one of the preferred applications of the cartridge assembly 1200 each of the vessels is filled with a series of related drugs at the factory for a particular application. For example, a series of medications that would be used for anesthesia, infarction, stroke or any other anticipated situation where several medications are used during a session of treatment.

Figure 26:
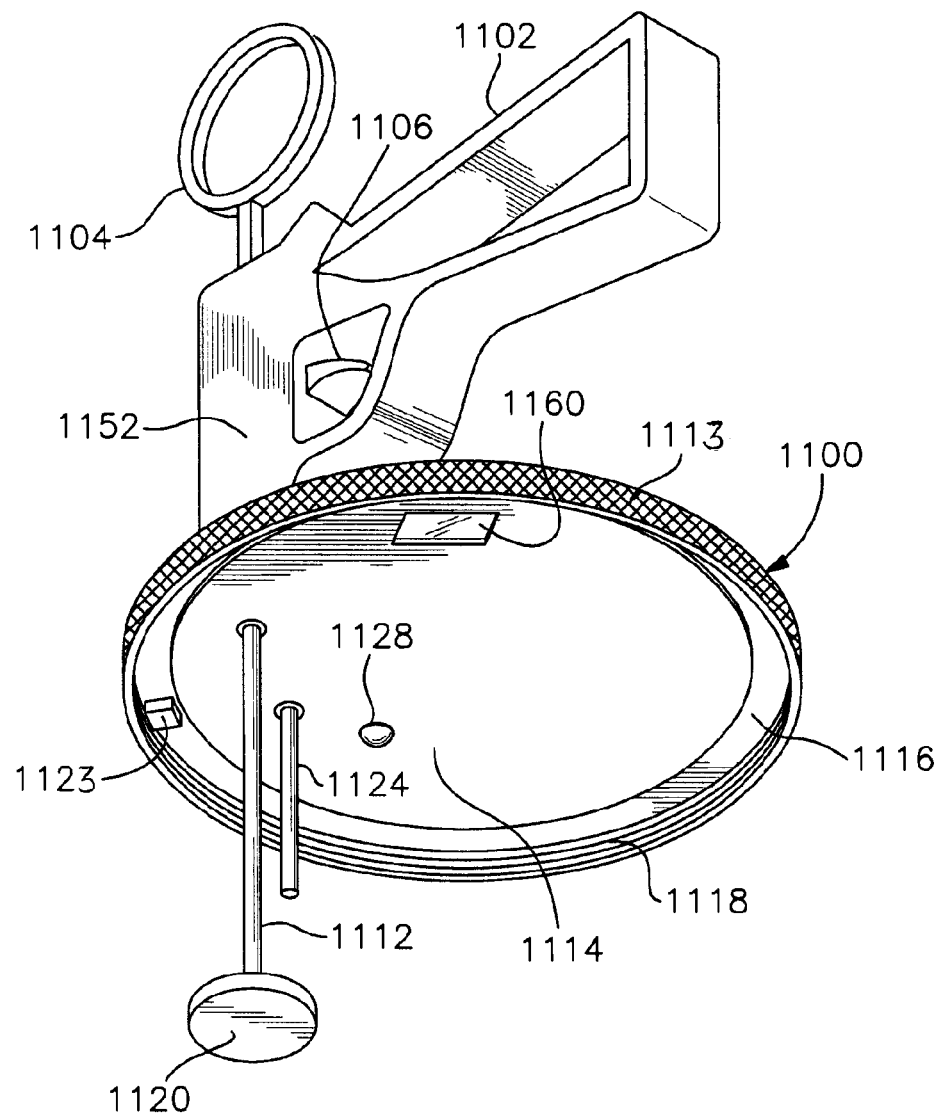
FIG. 26 is a perspective view of an alternate embodiment of a manual head assembly.

FIG. 26 shows an alternate embodiment of a manual head assembly 1100 that comprises, inter alia, a handle 1102, a case 1152, a trigger 1106, a cocking lever 1104 a key 1123, a shaft 1112, a head 1120, a shaft 1124, a spring button 1128, a base plate 1114, a seat 1116, threads 1118, a grip 1113 and a port 1160. In typical use said head assembly 1100 is attached to a case assembly, for example a case assembly similar to the case assembly 500 shown in FIG. 4. The seat 1116 rests on the seat 526 of the case assembly 500. The threads 1118 secure the head assembly 1100 to the case assembly 500. The grip 1113 is present to aid the user when tightening the threads 1118.

Said key 1123 is provided to aid in proper alignment of the head assembly 1100 with a case assembly. Said spring button 1128 snaps into divots 1204 on the cartridge assembly 1200 (shown in FIG. 25) when the shaft 1124 is aligned over said guide 1202 and said head 1120 is aligned over said piston 1206.

The case 1152 contains the mechanics of the head assembly 1100 that move the shaft 1112 and shaft 1124 and in a preferred embodiment can be materially similar to the mechanics shown in FIG. 9, with the addition of shaft 1124. Energy is introduced into the mechanics when the user pulls said cocking lever 1104. The shaft 1112 and shaft 1124 are released by pulling the trigger 1106. The handle 1102 provides a comfortable grip to the user and is optionally open to provide a means to hang the device, for example on an I.V. rack in an operating room.

The port 1160 is provided to allow the user to view the top side of a cartridge assembly 1200, seen in FIG. 25. Optionally a cartridge assembly may be labeled with the contents of each individual vessel so that when the port 1160 reveals an indicator then the head assembly 1100 is positioned to dispense a particular fluid. For example, when a drug name is seen through the port 1160 the device is positioned to dispense that drug. As the head assembly 1100 is rotated to deliver another fluid the port 1160 repositions over the indicator for the next fluid to be dispensed. Said port 1160 can simply be a cutout on the base plate 1114 or may optionally be comprised of a transparent material.

Figure 27:
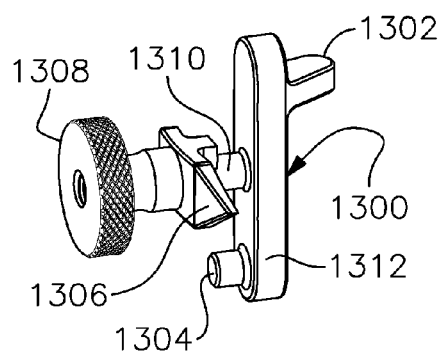
FIG. 27 is a perspective view of an alternate embodiment of a thumb lock assembly.
Figure 28:
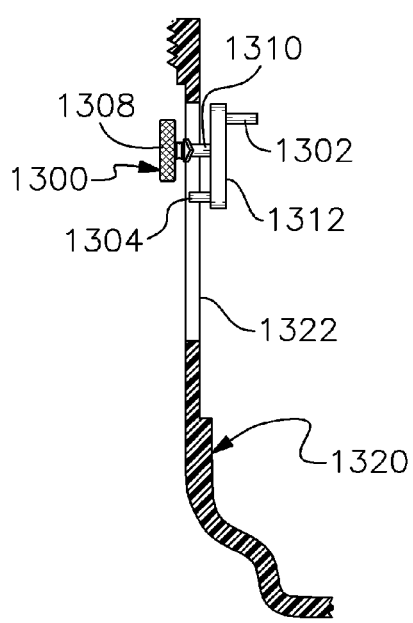
FIG. 28 is a cross-section elevation view of the thumb lock assembly shown in FIG. 27 in a case assembly.
Figure 29:
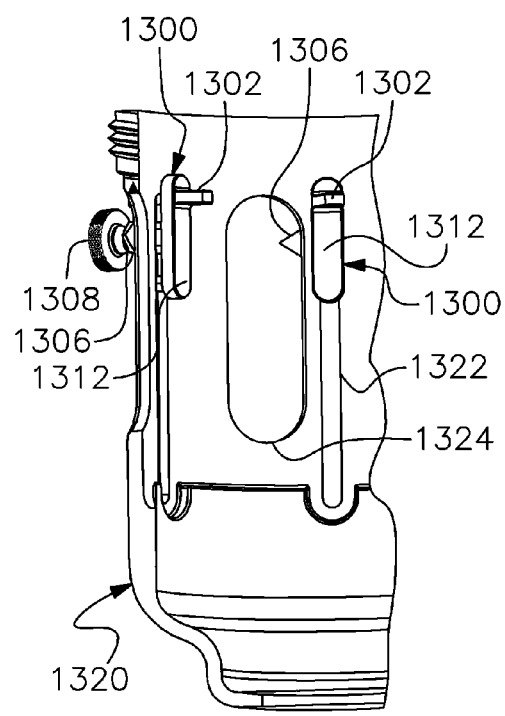
FIG. 29 is a cross-section perspective view of the thumb lock assembly shown in FIG. 27 in a case assembly.

FIGS. 27, 28 and 29 show generally a stop assembly 1300 and its relation to a case assembly 1320. The primary purpose of the stop assembly 1300 is to limit the amount of fluid dispensed. This stop assembly 1300 is particularly suited to the head assembly 1100 shown in FIG. 26. In typical use, the volume remaining in a drug vessel can be viewed though a port 1324 cut out of the side of a case assembly 1320. The user then loosens the stop assembly 1300 so that it can slide to the appropriate position on a track 1322 and the stop assembly 1300 securely tightened. The vessel then cannot be dispensed below the level indicated by the stop assembly 1300.

The stop assembly 1300 comprises, inter alia, a frame 1312, a guide 1304, a tab 1302, a neck 1310, an indicator 1306 and a thumb screw 1308. Said neck 1310 and said guide 1304 shuttle along a track 1322 in the case assembly 1320. The thumb lock 1308 can tighten the indicator 1306 against the outside of the case assembly 1320 and the frame 1312 against the inside wall of the case assembly 1320 thereby preventing the stop assembly 1300 from moving. The indicator 1306 is positioned so that it points to the edge of a port 1324 on the case assembly 1320. In typical use a user secures the stop assembly 1300 to the case assembly 1320 at the point along the track 1322 where the indicator 1306 is pointing to the level in the vessel where the user wishes to stop dispensation.

The tab 1302 interacts with the shaft 1124. The shaft 1124 passes through the guide 1202 that passes through the cartridge assembly 1200. While dispensing fluid the shaft 1112 presses the piston 1206 thus pressing the fluid out of the device while simultaneously the shaft 1124 descends into the guide 1202. To physically stop the fluid from further dispensing at the selected point the shaft 1112, shaft 1124 and the tab 1302 are dimensioned appropriately so that the shaft 1124 comes into contact with the tightened down tab 1302 at the same point where the shaft 1112 has pressed the top of the fluid being dispensed to the level indicated by the indicator 1306. In the preferred embodiment of the device there is one stop assembly 1300 for each of the dispensed fluids.

Figure 30:
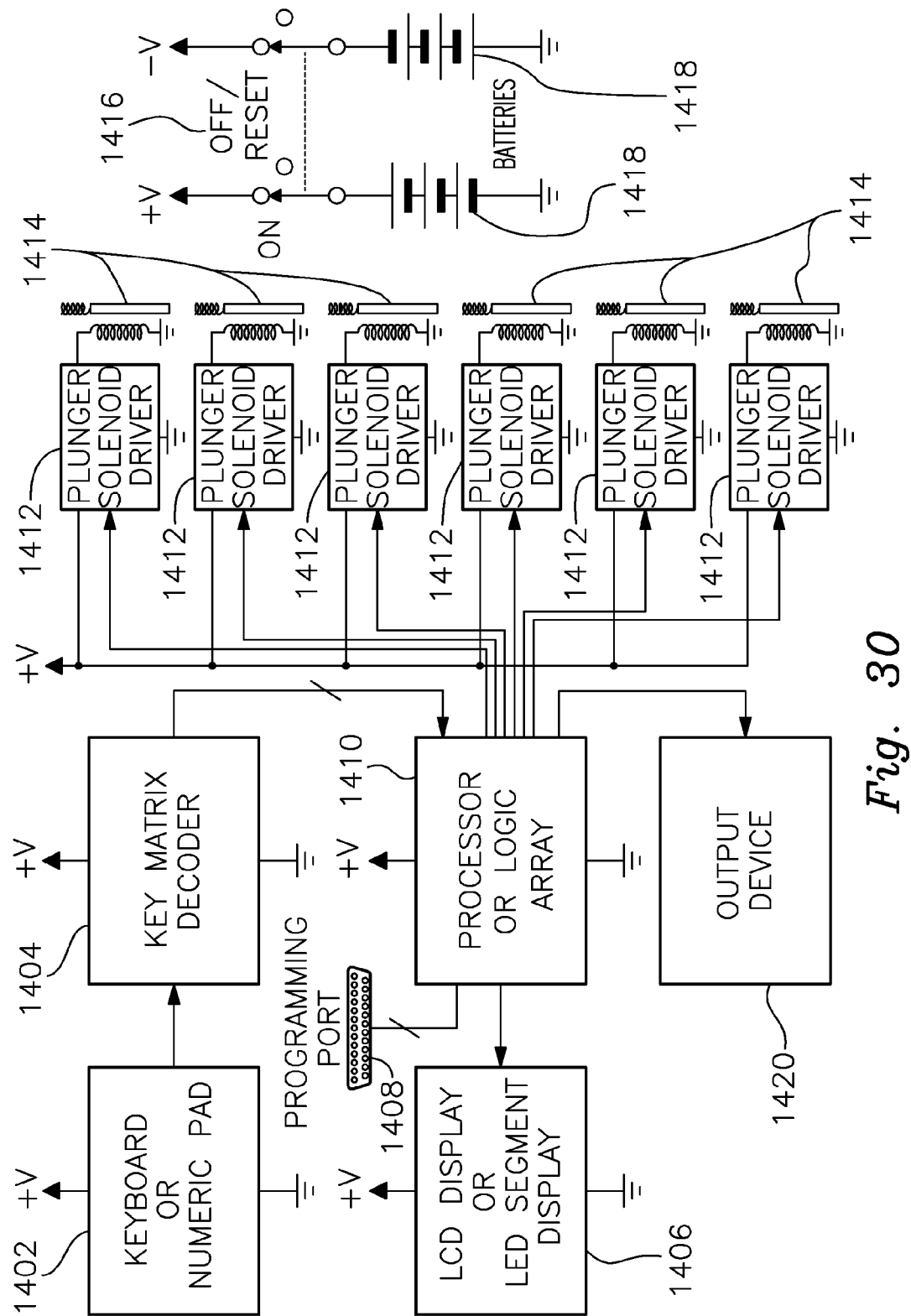
FIG. 30 is a circuit diagram of an alternate embodiment of a head assembly such as the electronic head assembly shown in FIG. 24.
Figure 31:
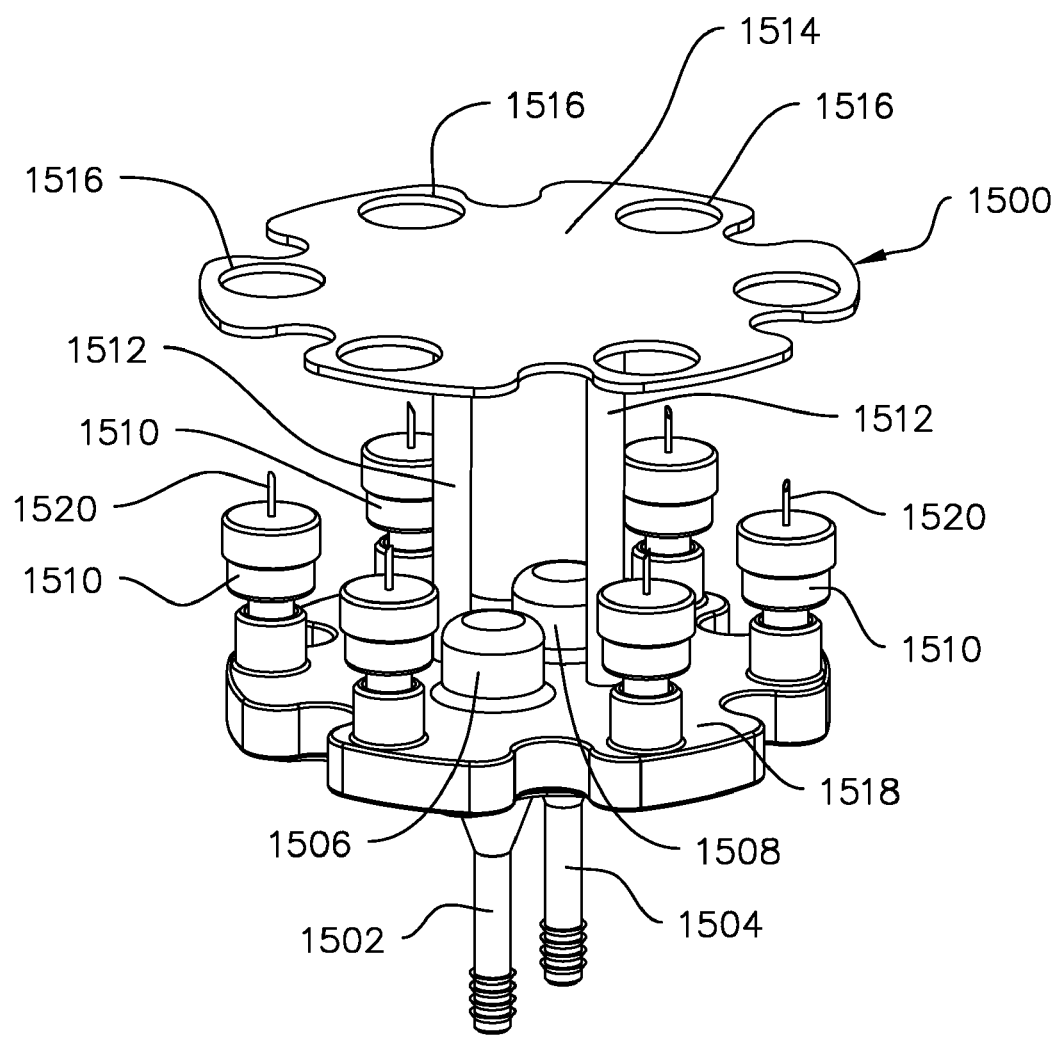
FIG. 31 is a perspective view of an alternate embodiment of a cartridge assembly.
Figure 32:
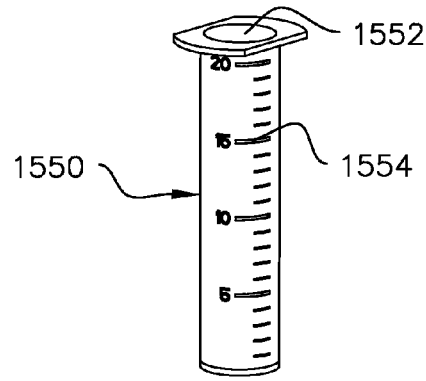
FIG. 32 is a perspective view of a vessel.
Figure 33:
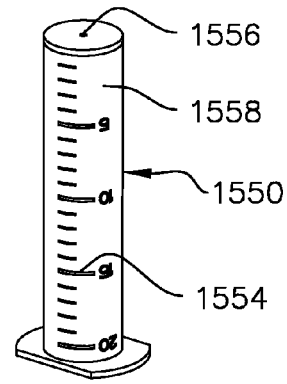
FIG. 33 is a perspective view of a vessel.
Figure 34:
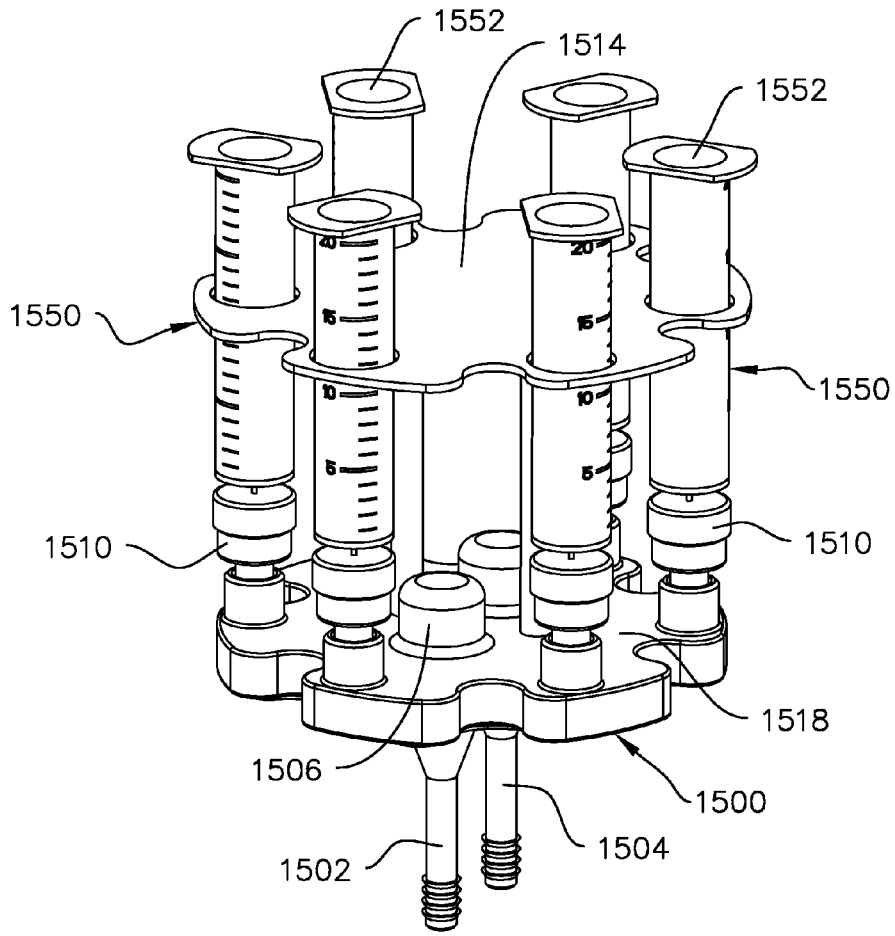
FIG. 34 is a perspective view of an alternate embodiment of a cartridge assembly.

FIG. 30 is an example of a circuit configuration for an electronic head assembly such as that shown in FIG. 24. This is but one example and many suitable variations are possible to produce more or less the desired functionality of the device. This circuit comprises, inter alia, an input device 1402 that could be for example a keypad, buttons or dials, a decoder 1404 to interface between said input device 1402 and a processor 1410. Said processor 1410 optionally sends data to a display 1406 and/or an output device 1420 such as a printer or removable memory module. Also optionally connected to the processor 1410 is a port 1408 that can be used to interface the processor 1410 with another computer to perform functions, such as for example, provide auxiliary power, remote monitoring, programming dispensing sequences, diagnostics or other functions. The processor controls a set of lineal actuators 1414 through a driver 1412. In a preferred embodiment there is a lineal actuator for each of the fluids dispensed, typically six. The head assembly is powered by batteries 1418 or externally through the port 1408 and can be turned on and off by a switch 1416.

FIGS. 31, 32, 33 and 34 demonstrate an alternate embodiment of a cartridge assembly 1500 and a vessel assembly 1550 that comprise, inter alia, a frame 1514, studs 1512, frame 1518, guides 1516, valves 1510, lances 1520, trap 1508, trap 1506, port 1502 and port 1504. Said frame 1518 is similar to the manifold assembly shown in FIG. 22 in that the preferred method of use a saline solution enters port 1502 and passes through a channel (not visible in FIG. 31 or 32) similar to the channel 858 (shown in FIG. 22) past each of the valves 1510 then exiting the cartridge assembly through said port 1504. Bubble traps 1506 reduce the number of bubbles that are dispensed with the primary fluid dispensed. On frame 1518 are studs that support frame 1514. Frame 1514 has a series of guides 1516 about the periphery that aid in securing said vessel assembly 1550 to said cartridge assembly 1500.

Said vessel assemblies 1550 are comprised of, inter alia, sidewall 1558, septum 1556, graduations 1554 and a piston 1552. Said graduations 1554 aid the user in determining the volume of fluid contained in the interior of the vessel assembly 1550 and are printed on or formed into the sidewall 1558. The top of the vessel assembly 1550 is sealed with a piston 1552. The opposing end has a septum 1556 that is forced onto said lance 1520 opening up the interior of the vessel assembly 1550 to said valve 1510. Said piston 1552 is forced into the interior of the vessel assembly 1550 thereby dispensing the fluid contained therein by means of any of the head units and case assemblies described above. The valves 1510 may be unidirectional to prevent back flow into the vessel assembly 1550.

The foregoing description conveys the best understanding of the objectives and advantages of the present invention.

Different embodiments may be made of the inventive concept of this invention. It is to be understood that all matter disclosed herein is to be interpreted merely as illustrative, and not in a limiting sense.

What is claimed is:

1. A fluid medication dispensing device, consisting of:
   A) an electronic head assembly comprising a case having a base, said base having a plurality of lineal actuators mounted thereon, each of said plurality of lineal actuators having a shaft extending therefrom that terminates as a head, said shaft retractably extends through and below said base, said electronic head assembly also comprising selecting means to select a fluid medication to be dispensed and dispensing means to dispense said fluid medication;
   B) a case assembly that contains a removable cartridge assembly of multiple said fluid medication to be dispensed, said removable cartridge assembly comprises a plurality of pistons, said plurality of pistons have a respective plurality of vessels by which said fluid medication travels through, said case assembly further comprises a manifold assembly, said manifold assembly comprises a body having a plurality of ports, each of said plurality of ports having a one-way valve and terminates as a receiver, each said receiver aligns with its respective said plurality of vessels, said body also comprises channel, first and second traps, and first and second chambers, said first and second traps contain gas bubbles in said fluid medication while traveling through said manifold assembly from said first chamber and before exiting said manifold assembly through said second chamber, said plurality of vessels are unified into said cartridge assembly that is removable from said case assembly, said first chamber serves as an intake port for an external fluid source to flush fluids through said manifold assembly, each said one-way valve is positioned in between said body and each respective said receiver;
   C) a processor, said processor serves as a primary controller of said electronic head assembly, said processor has an input device and a display, said selecting means comprises said processor controlling said plurality of lineal actuators to dispense said fluid medication as said dispensing means; and
   D) a mechanical means to stop dispensing of said fluid medication.

2. The fluid medication dispensing device set forth in claim 1, further characterized in that said fluid medication are drugs pre-selected for a specific medical procedure.

* * * * *